(12) United States Patent
Capobianco et al.

(10) Patent No.: US 8,088,631 B2
(45) Date of Patent: Jan. 3, 2012

(54) LANTHANIDE-DOPED NAYF$_4$ NANOCRYSTALS, METHOD OF PREPARING AND USES THEREOF

(75) Inventors: John A. Capobianco, Outremont (CA); John-Christopher Boyer, Montreal (CA); Louis A. Cuccia, Dorval (CA); Fiorenzo Vetrone, Montreal (CA)

(73) Assignee: Valorbec, Société en Commandite, Montreal (CA)

( * ) Notice: Subject to any disclaimer, the term of this patent is extended or adjusted under 35 U.S.C. 154(b) by 603 days.

(21) Appl. No.: 12/125,201

(22) Filed: May 22, 2008

(65) Prior Publication Data

US 2009/0042314 A1     Feb. 12, 2009

Related U.S. Application Data

(60) Provisional application No. 60/939,475, filed on May 22, 2007.

(30) Foreign Application Priority Data

May 22, 2007 (CA) .................................... 2589575

(51) Int. Cl.
*G01N 33/553* (2006.01)
(52) U.S. Cl. ...................................................... 436/525
(58) Field of Classification Search ................ 436/425
See application file for complete search history.

(56) References Cited

U.S. PATENT DOCUMENTS

| | | |
|---|---|---|
| 2003/0030067 A1 | 2/2003 | Chen |
| 2005/0014283 A1 | 1/2005 | Matsuura et al. |

FOREIGN PATENT DOCUMENTS

| | | |
|---|---|---|
| EP | 0 569 257 A1 | 11/1993 |
| WO | WO 99/29801 A1 | 6/1999 |
| WO | WO 01/86299 A2 | 11/2001 |
| WO | WO 03/087259 A1 | 10/2003 |

(Continued)

OTHER PUBLICATIONS

Aebischer et al. "Visible light emission upon near-infrared excitation in a transparent solution of nanocrystalline . . . " Chem. Phys. Lett., 407:124-128, 2005 (on web Apr. 7, 2005).

(Continued)

*Primary Examiner* — Mark Shibuya
*Assistant Examiner* — Pensee Do
(74) *Attorney, Agent, or Firm* — Goudreau Gage Dubuc

(57) ABSTRACT

The present invention relates to a method of preparing lanthanide-doped NaYF$_4$ nanocrystals, the method comprising: (A) providing a first solution comprising a non-coordinating solvent, a fatty acid coordinating ligand, sodium trifluoroacetate, yttrium trifluoroacetate, a first doping lanthanide trifluoroacetate and a second doping lanthanide trifluoroacetate, and a second solution comprising the non-coordinating solvent and the fatty acid coordinating ligand, the first and second solutions being substantially free of water and oxygen; (B) in an inert atmosphere, slowly adding the first solution heated at a temperature between about 100° C. and about 150° C. to the second solution heated at temperature between about 290° C. and about 330° C., thereby producing a reaction mixture containing the nanocrystals; and (C) recovering the nanocrystals from the reaction mixture. The invention also relates to lanthanide-doped uniformly shaped cubic NaYF$_4$ nanocrystals having an average particle size of at most about 50 nm with a standard deviation of at most about 15%. Finally, the invention also relates to methods of (A) identifying or authenticating a product, (B) labelling an analyte, (C) detecting an analyte, and (D) producing a light source for the telecommunication industry using the above nanocrystals.

31 Claims, 15 Drawing Sheets

FOREIGN PATENT DOCUMENTS

| | | |
|---|---|---|
| WO | WO 2004/058914 A1 | 7/2004 |
| WO | WO 2006/047621 A1 | 5/2006 |

OTHER PUBLICATIONS

Auzel et al. "Upconversion and Anti-Stokes Processes with f an d Ions in Solids" Chem. Rev., 104:139-173, 2004 (on web Nov. 18, 2003).

Boyer et al. "Synthesis of Colloidal Upconverting NaYF4 Nanocrystals Doped . . . " Talk at the 89th Canadian Chemistry Conference. May 27-31, 2006 (on web May 9, 2006).

Corstjens et al. "Infrared up-converting phosphors for bioassays" IEE Proc. Nanobiotechnol., 152:64-72, 2005.

Denk et al. "Two-Photon Laser Scanning Fluorescence Microscopy" Science, 248:73-76, 1990.

Hampl et al. "Upconverting Phosphor Reporters in Immuno-chromatographic Assays" Anal. Biochem., 288:176-187, 2001.

Heer et al. "Highly Efficient Multicolour Upconversion Emission in Transparent Colloids of Lanthanide-Doped NaYF4 . . . " Adv. Mater., 16:2102-2105, 2004 and supporting information.

Hirai et al. "Preparation of yttrium oxysulfide phosphor nanoparticles with infrared-to-green and -blue upconversion . . . " J. Colloid Interface Sci., 273:470-477, 2004.

Konig, K. "Multiphoton microscopy in life sciences" Microsc., 200, Pt 2:83-104, 2000.

Kramer et al. "Hexagonal Sodium Yttrium Fluoride Based Green and Blue Emitting Upconversion Phosphors" Chem. Mater., 16:1244-1251, 2004 (on web Mar. 2, 2004).

Kuningas et al. "Homogeneous Assay Technology Based on Upconverting Phosphors" Anal. Chem., 77:7348-7355, 2005 (on web Oct. 6, 2005).

Kuno et al. "The band edge luminescence of surface modified CdSe nanocrystallites: Probing the luminescing state" J. Chem. Phys., 106:9869-9882, 1997.

Larson et al. "Water-Soluble Quantum Dots for Multiphoton Fluorescence Imaging in Vivo" Science, 300:1434-1436, 2003.

Lim et al. "In Vivo and Scanning Electron Microscopy Imaging of Upconverting Nanophosphors in *Caenorhabditis elegans*" Nano Lett., 6:169-174, 2006 (on web Dec. 23, 2005).

Lu et al. "Synthesis and characterization of multi-functional nanoparticles possessing magnetic, . . . " J. Mater. Chem., 14:1336-1341, 2004 (on web Mar. 4, 2004).

Mai et al. "High-Quality Sodium Rare-Earth Fluoride Nanocrystals: Synthesis . . . " J. Am. Chem. Soc. 128:6426-6436, 2006 and supporting information (on web Apr. 20, 2006).

Niedbala et al."Detection of Analytes by Immunoassay Using Up-Converting Phosphor Technology" Anal. Biochem., 293:22-30, 2001 (on web May 4, 2001).

Page et al. "Upconversion-pumped luminescence efficiency of rare-earth-doped hosts sensitized with trivalent ytterbium" J. Opt. Soc. Am. B, 15:996-1008, 1998.

Park et al. "Ultra-large-scale syntheses of monodisperse nanocrystals" Nat. Mater., 3:891-895, 2004 (on web Nov. 28, 2004).

Pol et al. "Fluorescence Studies on Europium Doped Sodium-Yttrium Fluoride Phosphors" Indian J. Pure Appl. Phys., 11:886-8, 1973.

Pollnau et al. "Power dependance of upconversion luminescence in lanthanide and transition-metal-ion systems" Phys. Rev. B, 61: 3337-3346, 2000.

Reddy et al. "Growth and X-ray study of NaYF4 crystals" J. Mater. Sci. Lett., 2:83-84, 1983.

Rijke et al. "Up-converting phosphor reporters for nucleic acid microarrays" Nat. Biotechnol., 19:273-276, 2001.

Rillings et al. "A thermal stydy of the trifluoroacetates and pentafluoropropionates of praseodymium, samarium and erbium" Thermochim. Acta, 10:285-98, 1974.

Roy et al. "Controlled Massively Defective Crystalline Solutions with the Fluorite Structure" J. Electrochem. Soc., 111:421-429, 1964.

Russel, C. "Preparation of LiF, CaF2 and YF3 by thermal decomposition of the metal trifluoroacetates" Mater. Sci. Lett., 11:152-154, 1992.

Russel, C. "A pyrolytic route to fluoride glasses. I. Preparation and thermal decomposition of metal trifluoroacetates" Non-Cryst. Solids, 152:161-166, 1993.

Sachleben et al. "NMR studies of the surface structure and dynamics of semiconductor nanocrystals" Chem. Phys. Lett., 198:431-436, 1992.

Scheps, R. "Upconversion Laser Processes" Prog. Quant. Electr., 20:271-358, 1996.

Sivakumar et al. "Bright White Light through Up-Conversion of a Single NIR Source from Sol-Gel-Derived thin . . . " J. Am. Chem. Soc., 127:12464-12465, 2005 (on web Aug. 18, 2005).

Sudarsan et al. "General and Convenient Method for Making Highly Luminescent Sol-Gel Derived Silica . . . " Chem. Mater., 17:4736-4742, 2005 (on Web Aug. 12, 2005).

Suyver et al. "Highly efficient near-infrared to visible up-conversion process in NaYF4:Er3+, Yb3+" Lumin., 114:53-59, 2005 (on Web Jan. 5, 2005).

Suyver et al. "Novel materials doped with trivalent lanthanides and transition metal ions showing near-infrared . . . " Opt. Mater., 27:1111-1130, 2005 (on Web Jan. 20, 2005).

Wagener et al. "A pyrolytic route to fluoride glasses. II. Preparation of glasses in the system ZrF4-BaF2-LaF3-AlF3-NaF" Non-Cryst. Solids, 152:167-171, 1993.

Wang et al. "A general strategy for nanocrystal synthesis" Nature, 437, 121-124, 2005 and supporting information.

Wang et al. "Fluorescence Resonant Energy Transfer Biosensor Based on . . . " Angew. Chem., Int. Ed., 44, 6054-6057, 2005 and supporting information (on Web Aug. 24, 2005).

Wang et al. "Green upconversion nanocrystals for DNA detection" Chem. Commun., 2557-2559, 2006 and supplementary material (May 17, 2006).

Wang, "Transmission Electron Microscopy of Shape-Controlled Nanocrystals and Their Assemblies" J. Phys. Chem. B, 104, 1153-1175, 2000 (on Web Jan. 11, 2000).

Wei, et al. "Synthesis of Oil-Dispersible Hexagonal-Phase and Hexagonal-Shaped NaYF4: Yb, Er Nanoplates", Chem. Mater, 18, 5733-5737, 2006 (on Web on Oct. 25, 2006).

Yi et al. "Synthesis, Characterization, and Biological Application of Size-Controlled Nanocrystalline NaYF4:Yb, . . . " Nano Letters, 4:2191-2196, 2004 (on Web Oct. 16, 2004).

Yu et al. "Formation of High-Quality CdS and Other II-VI Semiconductor Nanocrystals . . . " Angew. Chem. Int. Ed., 41:2368-2371, 2002.

Zeng et al. "Synthesis and Upconversion Luminescence of Hexagonal-Phase NaYF4:Yb, Er3+ Phosphors of Controlled Size" Adv. Mater., 17:2119-2123, 2005 (on Web Jun. 30, 2005).

Zhang et al. "Single-Crystalline and Monodisperse LaF3 Triangular Nanoplates . . . " J. Am. Chem. Soc., 127, 3260-3261, 2005 and supporting information (on web Feb. 17, 2005).

Zijlmans et al. "Detection of Cell and Tissue Surface Antigens Using Up-Converting Phosphors . . . " Anal. Biochem., 267, 30-36, 1999.

LANTHANIDE-DOPED NAYF₄ NANOCRYSTALS, METHOD OF PREPARING AND USES THEREOF

CROSS REFERENCE TO RELATED APPLICATIONS

This application claims priority, under 35 U.S.C. §119(e), of U.S. provisional application Ser. No. 60/939,475, filed on May 22, 2007. All documents above are incorporated herein in their entirety by reference.

FIELD OF THE INVENTION

The present invention relates to lanthanide-doped NaYF$_4$ nanocrystals, method of preparing and uses thereof. More specifically, the present invention is concerned with cubic NaYF$_4$ nanocrystals and their production by thermal decomposition of trifluoroacetate precursors.

BACKGROUND OF THE INVENTION

Upconversion is a process where low-energy light, usually near-infrared (NIR) or infrared (IR), is converted to higher energies, ultraviolet (UV) or visible, via multiple absorptions or energy transfers (Scheps et al. Prog. Quant. Electr. 1996, 20, 271-358 and Auzel et al. Chem. Rev. 2004, 104, 139-173). This phenomenon has been observed in transition metal, lanthanide, and actinide ions doped into a solid-state host, though the highest efficiencies are found in lanthanide-doped materials.

Recent publications have reported upconversion from colloids of either cubic (α) or hexagonal (β) NaYF$_4$ nanocrytals (Heer et al. Adv. Mater. 2004, 16, 2102-2105; Zeng et al. Adv. Mater. 2005, 17, 2119-2123; Aebischer et al. Chem. Phys. Lett. 2005, 407, 124-128; and Suyver et al. Opt. Mater. 2005, 27, 1111-1130). To date, the highest upconversion efficiencies observed have been in hexagonal-phase NaYF$_4$ bulk materials doped with the Er$^{3+}$/Yb$^{3+}$ or Tm$^{3+}$/Yb$^{3+}$ ion couples synthesized via solid-state methods (Kramer et al. Chem. Mater. 2004, 16, 1244-1251 and Suyver et al. Lumin. 2005, 114, 53-59).

Colloids of upconverting NaYF$_4$ nanocrystals have been synthesized through thermal decomposition, precipitation, and high-pressure reactions. (Heer et al. Adv. Mater. 2004, 16, 2102-2105; Suyver et al. Opt. Mater. 2005, 27, 1111-1130; Zeng et al. Adv. Mater. 2005, 17, 2119-2123; Mai et al. J. Am. Chem. Soc. 2006, 128, 6426-6436; and Aebischer et al. Chem. Phys. Lett. 2005, 407, 124-128).

Other methods for producing NaYF$_4$ nanocrystals as well as other nanocrystals includes that described by Zhang et al. J. Am. Chem. Soc. 2005, 127, 3260; Mai et al. J. Am. Chem. Soc. 2006, 128(19), 6426; Wang et al. Nature 2005, 437, 121; Wang et al. Chem. Commun. 2006, 2557; Yi et al. Nano Letters 2004, 4, 2191; and Yi et al. WO 03/087259 published on Oct. 23, 2003. Method of producing bigger particles, which are therefore not nanocrystals are also known: Sanjurjo et al. WO 99/29801 published on Jun. 17, 1999.

The synthesis and spectroscopy of upconverting nanocrystals has garnered a tremendous amount of attention recently due, among other, to their potential use as biolabels and in biological assays (Heer et al. Adv. Mater. 2004, 16, 2102-2105; Lu et al. J. Mater. Chem. 2004, 14, 1336-1341; Yi et al. Nano Lett. 2004, 4, 2191-2196; Sivakumar et al. J. Am. Chem. Soc. 2005, 127, 12464-12465; Suyver et al. Opt. Mater. 2005, 27, 1111-1130; Wang et al. Angew. Chem., Int. Ed. 2005, 44, 6054-6057; Zeng et al. Adv. Mater. 2005, 17, 2119-2123; Mai et al. J. Am. Chem. Soc. 2006, 128, 6426-6436; Wang and Li, Chem. Comm. 2006, 24, 2557-2559; and Aebischer et al. Chem. Phys. Lett. 2005, 407, 124-128). Upconverting phosphors have a number of properties that make them attractive for use in these tasks (Kuningas et al. Anal. Chem. 2005, 77, 7348-7355; Corstjens et al. IEEE Proc. Nanobiotechnol. 2005, 152, 64-72; Hirai et al. J. Colloid Interface Sci. 2004, 273, 470-477; Rijke et al. Nat. Biotechnol. 2001, 19, 273-276; Hampl et al. Anal. Biochem. 2001, 288, 176-187; and Zijlmans et al. Anal. Biochem. 1999, 267, 30-36).

Upconverting NaYF$_4$ nanocrystals doped with Er$^{3+}$/Yb$^{3+}$ have already been successfully applied to analyte and DNA detection (Wang et al. Angew. Chem., Int. Ed. 2005, 44, 6054-6057 and Wang and Li, Chem. Comm. 2006, 24, 2557-2559). The use of upconverting nanophosphors for bioimaging has also been demonstrated (Lim et al. Nano Lett. 2006, 6, 169-174). The majority of current commercialized labels, such as organic dyes and quantum dots (QDs), utilize the Stokes luminescence of the fluorophore under UV, blue, or green excitation in order to detect the analyte. This leads to high background signals and difficulty in choosing an appropriate label because many biological species fluoresce under ultraviolet or visible radiation. The use of upconverting nanocrystals, two-photon dyes, or two-photon QDs removes many of these difficulties (Konig, J. Microsc. 2000, 200, 83-104; Larson et al. Science 2003, 300, 1434-1437; Kuningas et al. Anal. Chem. 2005, 77, 7348-7355; Hirai et al. J. Colloid Interface Sci. 2004, 273, 470-477; Hampl et al. Anal. Biochem. 2001, 288, 176-187; Corstjens, et al. IEEE Proc.-Nanobiotechnol. 2005, 152, 64-72; Niedbala et al. Anal. Biochem. 2001, 293, 22-30; Rijke et al. Nat. Biotechnol. 2001, 19, 273-276; and Denk et al. Science 1990, 248, 73-76). However, the drawback of using dyes or quantum dots is that they require expensive pulse lasers to meet the high power densities necessary to obtain the two-photon effect (Konig, J. Microsc. 2000, 200, 83-104; Larson et al. Science 2003, 300, 1434-1437; Rijke et al. Nat. Biotechnol. 2001, 19, 273-276; and Denk et al. Science 1990, 248, 73-76). In contrast, due to the relative high efficiency of the upconversion process in lanthanide-doped materials, inexpensive 980 nm NIR diode lasers may be employed as the excitation source. The realization of efficient NIR to visible upconverting nanocrystals will therefore unlock a realm of new possibilities in the field of biolabeling and bioassays.

However, at this point, there remains a need for nanocrystals, more particularly NaYF$_4$ nanocrystals, that have improved physical characteristics over that described in the prior art. In fact, it has been shown that the optical properties of nanocrystals are related to their particle size. Thus, smaller nanocrystals are needed. Also, the particle size distribution as well as the shape and the surface of the nanocrystals are related to the ease of producing a colloidal solution of these nanocrystals, to the transparence and stability of this solution and to the quality, reproducibility and uniformity of the spectral response of the nanocrystals. Thus, nanocrystals with uniform particle size and shape are also needed.

The present description refers to a number of documents, the content of which is herein incorporated by reference in their entirety.

SUMMARY OF THE INVENTION

There is provided a method of preparing lanthanide-doped NaYF$_4$ nanocrystals, the method comprising: (A) providing a first solution comprising a non-coordinating solvent, a fatty acid coordinating ligand, sodium trifluoroacetate, yttrium trifluoroacetate, a first doping lanthanide trifluoroacetate and a second doping lanthanide trifluoroacetate, and a second solution comprising said non-coordinating solvent and said fatty acid coordinating ligand, said first and second solutions being substantially free of water and oxygen; (B) in an inert atmosphere, slowly adding the first solution heated at a temperature between about 100° C. and about 150° C. to the second solution heated at temperature between about 290° C. and about 330° C., thereby producing a reaction mixture containing said nanocrystals; (C) recovering said nanocrystals from said reaction mixture.

In an embodiment, the first and second doping lanthanides are erbium and ytterbium, or thulium and ytterbium.

In an embodiment, the method further comprises maintaining the reaction mixture at a temperature between about 290° C. and about 330° C. under the inert atmosphere before (C). In an embodiment, the maintaining step lasts at least about 1 hour.

In an embodiment, the first solution is added to the second solution in a small substantially steady stream. In an embodiment, the first solution is added to the second solution through a cannula. In an embodiment, the first solution is added to the second solution at a rate of at most about 10%/min.

In an embodiment, the fatty acid coordinating ligand is oleic acid.

In an embodiment, the non-coordinating solvent is octadecene.

There are also provided lanthanide-doped $NaYF_4$ nanocrystals produced by the above method. In an embodiment, the nanocrystals are uniformly shaped and have an average particle size of at most about 50 nm with a standard deviation of at most about 15%.

There are also provided lanthanide-doped uniformly shaped cubic nanocrystals having an average particle size of at most about 50 nm with a standard deviation of at most about 15%.

In an embodiment, the nanocrystals are $NaYF_4$: $Er^{3+}/Yb^{3+}$ or $NaYF_4$: $Tm^{3+}/Yb^{3+}$.

In an embodiment, the nanocrystals have a fatty acid coordinating ligand on a surface of the nanocrystals. In an embodiment, the fatty acid coordinating ligand is oleic acid.

In an embodiment, the average particle size is between about 25 and about 35 nm. In an embodiment, the standard deviation is at most about 4%. In an embodiment, at least about 90% of the nanocrystal have a hexagonal shape when observed by TEM.

In an embodiment, the nanocrystals are produced by the above-method.

There is also provided a method of identifying or authenticating a product, the method comprising the step of including the above nanocrystals as a marker in the product. In an embodiment, the product is an ink, a fuel, a paper, a cardboard, a polymer or a textile. In an embodiment, the nanocrystal are produced by the above method.

There is also provided a method of labelling an analyte, the method comprising contacting the analyte with the above nanocrystals, thereby permitting association of the analyte with the nanocrystals. In an embodiment, the nanocrystals are bound to the analyte. In an embodiment, the analyte is a biological target. In an embodiment, the nanocrystal are produced by the above method.

There is also provided a method of detecting an analyte, the method comprising: (A) providing an analyte which is associated with the above nanocrystals; and (B) detecting the analyte by stimulating the nanocrystals associated with the analyte. In an embodiment, the providing step comprises contacting the analyte with the nanocrystals, thereby permitting association of the analyte with the nanocrystals. In an embodiment, the nanocrystal are produced by the above method. In an embodiment, the nanocrystals are bound to the analyte. In an embodiment, the analyte is a biological target.

There is also provided a method of producing a light source for the telecommunication industry, the method comprising the step of stimulating the above nanocrystals with incoming light. In an embodiment, the nanocrystal are produced by the above method.

DETAILED DESCRIPTION OF THE INVENTION

In an aspect of the present invention, there is provided a method of preparing lanthanide-doped $NaYF_4$ nanocrystals which have very interesting properties that had not been obtained otherwise up to now.

The method of the invention comprises the steps of providing (A) a first solution comprising a non-coordinating solvent, a fatty acid coordinating ligand, sodium trifluoroacetate, yttrium trifluoroacetate, a first doping lanthanide trifluoroacetate and a second doping lanthanide trifluoroacetate, and (B) a second solution comprising the non-coordinating solvent and the fatty acid coordinating ligand, the first and second solutions being substantially free of water and oxygen.

The non-coordinating solvent is a solvent that will not form a coordination complex or a covalent link with the reactants or the nanocrystals. Non-limiting examples of such solvent include octadecene, eicosene, and terphenyl. In embodiments, this solvent may be octadecene.

The coordinating ligand is a fatty acid that will form a coordinate bond with the nanoparticles and coat their surface. In embodiments, this fatty acid may have more than 12 carbon atoms and comprise 0, 1 or more insaturations. Non-limiting examples of such fatty acid ligands include oleic acid, stearic acid and lauric acid. In embodiments, the ligand may be oleic acid.

The first and second doping lanthanides are lanthanide ions included in the $NaYF_4$ nanoparticles to provide them with the desired optical properties. In embodiments, the first and second doping lanthanides may be erbium and ytterbium, or thulium and ytterbium. In the first solution, sodium, yttrium and the doping lanthanides are all in the form of trifluoroacetates. This is to take advantage of the fact that metal trifluoroacetates thermally decompose to give the corresponding metal fluorides at relatively low temperatures. The reaction involved here is therefore the decomposition of sodium, yttrium and the doping lanthanides trifluoroacetates into sodium, yttrium and the doping lanthanides fluoride, i.e. $NaYF_4$: doping lanthanides.

Sodium trifluoroacetate is available commercially. As well known to the person of skill in the art, the doping lanthanides and yttrium trifluoroacetates can be synthesized from the corresponding lanthanides and yttrium oxides and trifluoroacetic acid, respectively.

The first and second solutions are substantially free of water and oxygen. As used herein, "substantially free of water and oxygen" or "free of water and oxygen" means that the solutions are sufficiently free of water and oxygen so that any remaining water or oxygen does not have a significant deleterious effect on the chemical reaction involved in the method. For example, the solutions can be considered to be (substantially) free of water and oxygen after being heated at a temperature between about 100° C. and about 150° C. under vacuum for a period of time sufficient to remove most of the oxygen and water, for example about 30 minutes.

The method of the invention then comprise the step of slowly adding the first solution heated at a temperature between about 100° C. and about 150° C. to the second solution heated at temperature between about 290° C. and about 330° C. thereby producing a reaction mixture containing the nanocrystals.

Without being bound by theory, the inventors believe that the decomposition of the trifluoroacetate precursors and thus the crystallization of the $NaYF_4$ particles occur quite fast at the temperature of the second solution (while there is no decomposition at the temperature of the first solution). The purpose of adding the first solution containing the trifluoroacetates slowly into the hotter second solution is thus the instantaneous (or at least the very fast) thermal decomposition of the trifluoroacetates upon addition. By adding the trifluoroacetates to the solution slowly, the inventors found that they can control the rate of decomposition and formation of the particles.

This results in the nanocrystals obtained having the very interesting and unexpected properties mentioned above. More specifically, the nanocrystals obtained are quite small, have a narrow size distribution and are uniformly shaped. In essence, by performing the addition slowly over a long period of time, the inventors found they can separate the nucleation and growth phases of the nanocrystals resulting in uniformly shaped nanocrystals with a narrow size distribution. All of theses are very desirable properties for many of these nanocrystals' applications.

In contrast, the inventors observed that if the trifluoroacetates (first solution) are added too fast to the second solution, the decomposition will be uneven and result in the nanocrystals being of different shape and having a wider size distribution.

This phenomenon is clearly illustrated in Comparative Example 1 below where all of the trifluoroacetate are added at once before heating the solution. In Comparative Example 1, the synthesis of $\alpha$-$NaYF_4$ nanoparticles in octadecene and oleic acid resulted in irregularly shaped particles with a wide particle size range. While, in Example 1, where the first solution is slowly added to the second solution, the TEM data clearly show that the slow addition of the first solution into the second solution unexpectedly results in $\alpha$-$NaYF_4$ nanoparticles with defined shapes and narrow size distributions.

In the present method, the first solution may be, for example, added to the second solution in a small substantially steady stream. As used herein, a "substantially steady" stream means a stream that is for the most part continuous but may be interrupted one or more time if desired. A "small" stream is a stream sufficiently small so that the decomposition of the trifluoroacetates will be instantaneous. This addition may be done using any suitable means known to the person of skill in the art, for example using a syringe. In embodiments, the first solution may be added to the second solution through a cannula.

Non-limiting examples where the first solution is slowly added to the second solution includes cases where it is added at a rate of at most about 10%/min, about 7%/min, or about 5%/min. However, the preferred rate of addition depends on the exact temperature of the second solution: higher temperatures allowing faster additions and lower temperatures favouring slower additions.

The adding step is carried out in an inert atmosphere, which is an atmosphere that will not interact with the reactant and reaction mixture. In the present invention, the inert atmosphere should be substantially free of water vapour and oxygen. Non-limiting examples of suitable inert atmosphere include nitrogen and argon.

Finally, the method comprises the step of recovering the nanocrystals from the reaction mixture. The nanocrystals can be recovered by any method commonly known to the person of skill in the art. For example, the nanocrystals may be precipitated and then isolated via centrifugation.

The method of the invention may further comprise the step of maintaining the reaction mixture at a temperature between about 290° C. and about 330° C. under the inert atmosphere before recovering the nanocrystals from the reaction mixture. More specifically, this maintaining step may last at least about 1 hour.

The present invention also relates to the lanthanide-doped $NaYF_4$ nanocrystals produced by the above-described method. These nanocrystals have the interesting and unexpected properties of being quite small, having a narrow size distribution and being uniformly shaped.

The method of the invention presents several advantages. First, it produces cubic $NaYF_4$ nanocrystals with the above-mentioned unexpected properties. Moreover, these nanocrystals are highly luminescent and capable of being excited with a 980 nm laser diode, which further increases their commercial usefulness. The nanocrystals are also usually capable of being colloidally dispersed in nonpolar solvent (e.g. hexane, toluene, dichloromethane). Furthermore, this method is very simple, uses technical-grade solvents and ligands and does not involve sophisticated equipment, which makes it very cost-effective. Finally, this method allows tailoring the size and shape of the synthesized nanoparticles by varying various synthetic parameters.

In accordance with the present invention, there is also provided lanthanide-doped uniformly shaped cubic $NaYF_4$ nanocrystals having an average particle size of at most about 50 nm with a standard deviation of at most about 15%.

As used herein "uniformly shaped" means that a major part of the nanocrystals have the same physical shape or appearance. More specifically, these nanocrystals may be truncated octahedron. Non-limiting examples of nanocrystals that are uniformly shaped include nanocrystals wherein at least about 75%, 85%, 90%, 95% or 98% of the nanocrystals have a hexagonal shape when observed by transmission electron microscopy (TEM). This hexagonal shape observed by TEM is the 2D projection of the above-mentioned 3D truncated octahedron nanocrystals.

The physical shape or appearance of the nanocrystals is different from their crystalline phase, which is cubic ($\alpha$).

The nanocrystals of the invention may be $NaYF_4$: $Er^{3+}$/$Yb^{3+}$ or $NaYF_4$: $Tm^{3+}$/$Yb^{3+}$.

The nanocrystals may have the above-described fatty acid coordinating ligand on their surface.

In embodiments, the average particle size of the nanocrystals may be between about 10 and about 40 nm, between about 20 and about 40 nm, between about 25 and about 35 nm, or may be about 27.6 nm and the standard deviation may be at most about 10%, 6%, 4%, or 3.3%.

These nanocrystals have several advantages. First, they are particularly robust and resistant to chemical and photo-induced degradation, which makes them ideal for many applications. Also, they are usually capable of being colloidally dispersed in various nonpolar organic solvents (e.g., hexane, toluene, dichloromethane), thus forming colloidally stable solutions. Moreover, they are usually highly luminescent nanoparticles capable of converting near-infrared into visible light. More specifically, they are able to emit visible light under 980 nm laser diode excitation via the upconversion process under relatively low excitation power densities. In fact, the colloids of the $Er^{3+}$, $Yb^{3+}$- and $Tm^{3+}$, $Yb^{3+}$-doped $NaYF_4$ nanocrystals usually exhibit green/red and blue upconversion luminescence, respectively, under 980 nm laser diode excitation with low power densities. The relatively low-cost laser diode used for excitation makes these nanocrystals very attractive for potential commercial applications.

The present invention also relates to methods of uses of the above-mentioned nanocrystals. These nanocrystals may find use in the security industry as well as in the military where they can be used, for example, as markers for the identification or authentication of products. In these applications, the nanocrystals would be included in the product during its fabrication. Then, for the purpose of identification, the product would be illuminated with a light at the correct wavelength to stimulate the nanocrystals. The stimulated upconverting nanocrystals will then emit tell-tale recognizable light at specific wavelengths and allow authenticating the product.

Non-limiting examples of products that could contain the nanocrystals include bank notes, checks, passports and other sensible documents, security inks, security papers, fuels, packaging (for pharmaceutical, spirits, controlled products and other products that are subject to counterfeiting or smuggling), and branded products. More specifically, the nanocrystals could be included in an ink or in a fuel or embedded in paper, cardboard, a polymer, a textile as well as other materials.

Furthermore, the nanocrystals can also be used as labels for the detection of an analyte. In this case, the nanocrystals could be associated with the analyte and detected via their light emission when appropriately stimulated. In embodiments, the label may be bound to the analyte. Also, the analyte can be a biological target. As used herein, "biological target" refers to any chemical moiety of biologic origin, compound, cellular or subcellular component which is associated with a biological function. Examples of "biological targets" include proteins (e.g., antibodies), nucleic acids (ADN, ARN, etc.), metabolites, cells, microorganisms, subcellular organelles, lipids, carbohydrates, glycolipids, antigens, and other biological molecules. An example of biological detection procedure using the nanocrystals would be FRET (Fluorescence Resonance Energy Transfer) analysis. In embodiments, the analyte, and especially the biological target, may be detected in vitro, in vivo, or ex-vivo.

The nanocrystals may be used as infra-red responsive biocompatible nanoparticles for advanced biomedical applications. The infra-red responsive nanoparticles will allow multiple activities, including cell targeting, imaging and therapeutic functionalities. The nanoparticles will be functionalized for bioactivity by attaching carefully selected biofunctional ligands or molecules on their surface, using biocompatible coatings.

Nanoparticles doped with lanthanide ions that emit in the infrared are also attractive to the telecommunication industry as light sources for this communication band (IR). In this case, the nanocrystals would be illuminated with a light at the correct wavelength to stimulate them and the stimulated upconverting nanocrystals will then emit the desired IR light.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
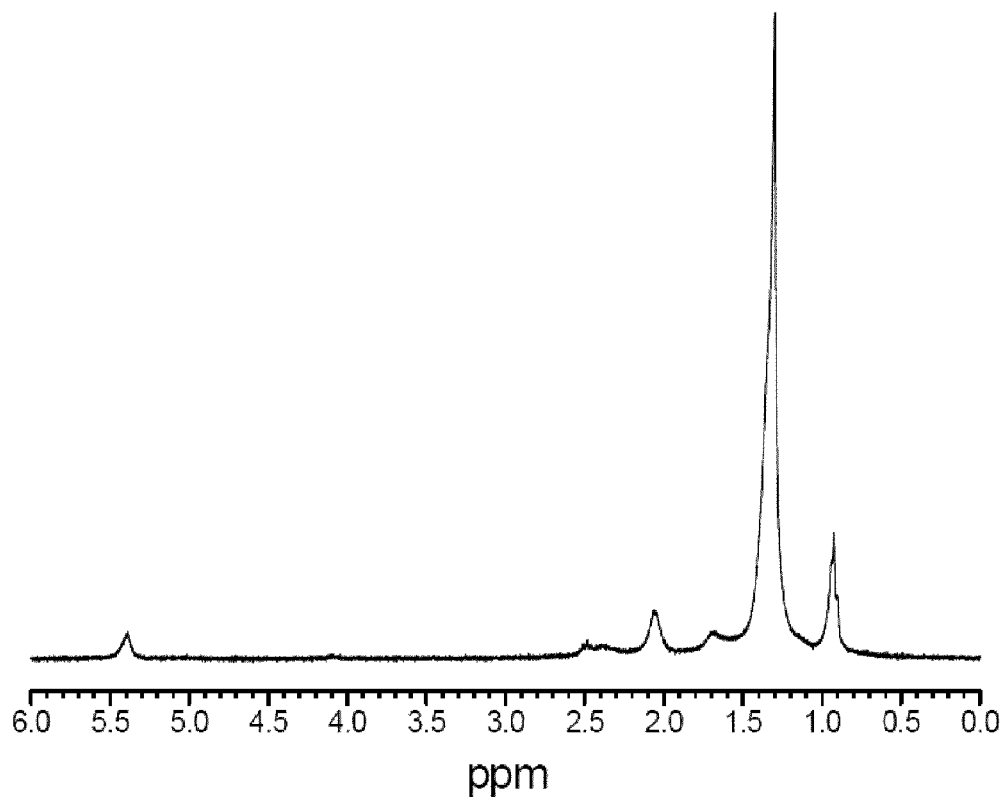
FIG. 1 is a $^1$H NMR spectrum of an undoped $NaYF_4$ sample dispersed in $CDCl_3$ recorded on a Varian 300 MHz spectrometer [Chemical shifts are reported in parts-per-million δ: 5.3-5.45 (broad, —HC═CH—), 2.0-2.1 (broad, $CH_3$—$(CH_2)_6$—$CH_2$—CH═CH—$CH_2$—$(CH_2)_6$—COOH), 1.2-1.4 (broad, —$(CH_2)_6$—) and 0.85-1.00 (broad, —$CH_3$)]

The present invention is illustrated in further details by the following non-limiting examples. In Comparative Example 1, the trifluoroacetates are heated up to a temperature at which they decompose. This produces nanocrystals that are not uniformly shaped and that have a wide size distribution. In contrast, in Example 1, the first solution containing the trifluoroacetates is added to the hot second solution and the decomposition occurs instantaneously. This produces uniformly shaped small nanocrystals with a narrow size distribution.

Comparative Example 1

NaYF$_4$ nanocrystals doped with Er$^{3+}$/Yb$^{3+}$ or Tm$^{3+}$/Yb$^{3+}$ ion couples were synthesized via the thermal decomposition of trifluoroacetate precursors in a high-boiling-point organic solvent. This procedure, like other procedures for producing LaF$_3$ nanoplates (Mai et al. J. Am. Chem. Soc. 2006, 128, 6426-6436 and Zhang et al. J. Am. Chem. Soc. 2005, 127, 3260-3261), take advantage of the fact that metal trifluoroacetates thermally decompose to give the corresponding metal fluorides at relatively low temperatures (200-300° C.) (Russel, Mater. Sci. Lett. 1992, 11, 152-154; Russel, Non-Cryst. Solids 1993, 152, 161-166; Wagener et al. Non-Cryst. Solids 1993, 152, 167-171; and Rillings et al. Thermochim. Acta 1974, 10, 285-98). In this method, non-coordinating solvent octadecene was used as the primary solvent because of its high boiling point (315° C.) and oleic acid was chosen as the coordinating ligand (Park et al. Nat. Mater. 2004, 3, 891-895; and Yu et al. Angew. Chem., Int. Ed. 2002, 41, 2368-2371). This synthetic route provided highly luminescent cubic NaYF$_4$ nanoparticles through a simple one-pot technique with only one preparatory step.

The lanthanide trifluoroacetate precursors were prepared from the corresponding lanthanide oxides and trifluoroacetic acid (Russel, Non-Cryst. Solids 1993, 152, 161-166). The corresponding amount of sodium trifluoroacetate was then added to the reaction vessel with octadecene and oleic acid. The resulting solution was heated to 100° C. under vacuum with stirring for 30 min to remove residual water and oxygen. The solution was then heated to 300° C. at a rate of 10° C./min under Ar and kept at this temperature for 1 h. Subsequently, the mixture was allowed to cool to room temperature, and the nanocrystals were precipitated by the addition of hexane/acetone (1:4 v/v) and isolated via centrifugation. The resulting pellet was then washed once with ethanol and further purified by dispersing in a minimum amount of chloroform and precipitated with excess ethanol. The resulting nanocrystals were dried under vacuum for 24 h.

A more detailed description of the synthetic procedure and spectroscopy setup is given below.

Synthesis of Ln$^{3+}$ doped NaYF$_4$ nanocrystals. All chemicals utilized in the synthesis of the nanocrystals were purchased from Aldrich. The lanthanide trifluoroacetate precursors were prepared from the corresponding lanthanide and yttrium oxides and trifluoroacetic acid (99%). In the case of the NaYF$_4$: Er$^3$+2 mol %, Yb$^3$+20 mol % codoped sample, 9.6 mg (0.025 mmol) of Er$_2$O$_3$, 98.5 mg (0.25 mmol) of Yb$_2$O$_3$, and 220.2 mg (0.975 mmol) of Y$_2$O$_3$ were dissolved in 10 mL of 50% aqueous trifluoroacetic acid at 80° C. The residual water and acid were then slowly evaporated to dryness at 50° C.

The 0.3400 g (2.5 mmol) of sodium trifluoroacetate (98%) was then added to the reaction vessel with 20 mL of octadecene (90%) and 20 mL of oleic acid (90%). The resulting solution was slowly heated to 100° C. under vacuum with magnetic stirring for 30 minutes to remove residual water and oxygen during which time the flask was purged periodically with dry argon gas. The resulting clear solution had a slight yellow color.

The solution was then heated to 300° C. at a rate of 10° C./min under dry argon and kept at this temperature for 1 hr. At approximately 250° C., the evolution of small gas bubbles was observed from the solution indicating the decomposition of the metal trifluoroacetates. A burst of nucleation was observed between 280-300° C. which resulted in the solution becoming turbid.

Subsequently, the mixture was allowed to cool to room temperature during which time the solution became clear and a yellow colloidal solution was obtained. The nanocrystals were precipitated by the addition of hexane/acetone (v/v in 1:4) and isolated via centrifugation at 3000 rpm corresponding to a relative centrifugal field (RCF) of approximately 1000. The resulting pellet was then washed once with ethanol and further purified by dispersing in a minimum amount of chloroform and precipitated with excess ethanol. The resulting nanocrystals were dried under vacuum for a minimum of 24 hrs.

The resulting nanocrystals could be dispersed in nonpolar solvents (e.g. hexane, toluene, dichloromethane) by sonicating a suspension of the nanocrystals in a bath sonicator for 10-20 minutes. It was sometimes necessary to add one or two drops of oleic acid to the suspension to aid in the dispersion of the nanocrystals. To eliminate this addition of oleic acid, it was preferable to leave the nanocrystals in a "muddy" state instead of the dry powder form.

NMR Measurements. The $^1$H NMR spectrum of an undoped NaYF$_4$ sample dispersed in CDCl$_3$ was recorded using a Varian 300 MHz spectrometer. The spectrometer frequency was 300.03 MHz and 128 transients were recorded. The residual proton signals of the deuterated solvents were used as internal standards (CDCl$_3$ $^1$H δ: 7.27 ppm).

Powder X-ray Diffraction Analysis. The powder diffraction patterns were collected at room temperature with the Kα (40 kV, 20 mA) radiation of Cu on a PW-1050 Philips diffractometer automated with the Difftech Sie-Ray system. Data accumulation and processing were carried out using the Difftech Sie-122 software. The scanning step size was 0.05° 2θ with a counting time of 10 s per step.

Transmission Electron Microscopy (TEM) Studies. TEM was performed on a NaYF$_4$: Er$^{3+}$ 2%, Yb$^{3+}$ 20% sample using a JEOL JEM-2000 FX microscope operating at 80 kV equipped with a charged-coupled device (CCD)-camera (Gatan). A small amount of the sample (~1 mg) was dispersed in 1 g of hexane to give an approximate 0.1 wt % solution. One drop of the resulting solution was evaporated on a formvar/carbon film supported on a 300 mesh copper grid (3 mm in diameter). High resolution TEM was performed on the same sample using a 200 KeV JEOL JEM-2100F microscope.

Visible and NIR Room Temperature Emission Spectroscopy ($\lambda_{exc}$=977 nm). The upconverted emission spectra were obtained using 977 nm radiation from a Spectra-Physics model 3900 Ti sapphire laser pumped by the 514.5 nm line of the Coherent Sabre Innova 20 W Argon Ion laser. For the upconversion studies, the samples were placed in 1 cm pathlength quartz cuvettes (Hellma, QS). The visible emissions were collected from the samples at $\pi/2$ from the incident beam and then dispersed by a 1 m Jarrell-Ash Czerny-Turner double monochromator. Resolution of the monochromator was 0.2 nm with slit widths of 200 µm. The visible emissions from the sample exiting the monochromator were detected by a thermoelectrically cooled Hamamatsu R943-02 photomultiplier tube and the photomultiplied signals were processed by a Stanford Research Systems (SRS) model SR440 preamplifier. A Stanford Research Systems model SR 400 gated photon counter data acquisition system was used as an interface between the spectroscopic equipment and the computer running the SRS SR 465 data acquisition software.

The presence of the oleic acid ligand on the surface of the nanocrystals was confirmed via the $^1$H NMR of an undoped NaYF$_4$ sample (FIG. 1). Due to the presence of the capping ligand, the nanocrystals could be dispersed in nonpolar solvents and were colloidally stable in solution for a period of weeks with no visible agglomeration or settling.

Figure 2:
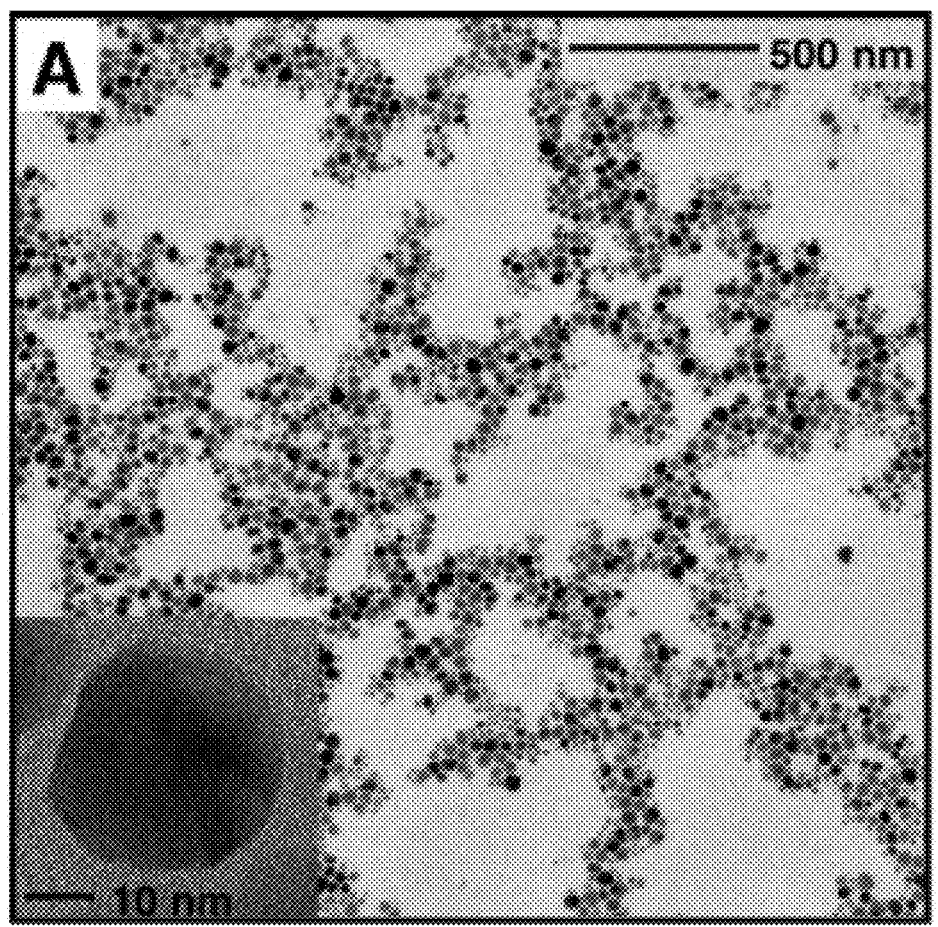
FIG. 2 is a transmission electron microscopy (TEM) image of $NaYF_4$: 2% $Er^{3+}$, 20% $Yb^{3+}$ nanocrystals [Inset: High-resolution TEM (HRTEM) image of a single nanocrystal.]
Figure 3:
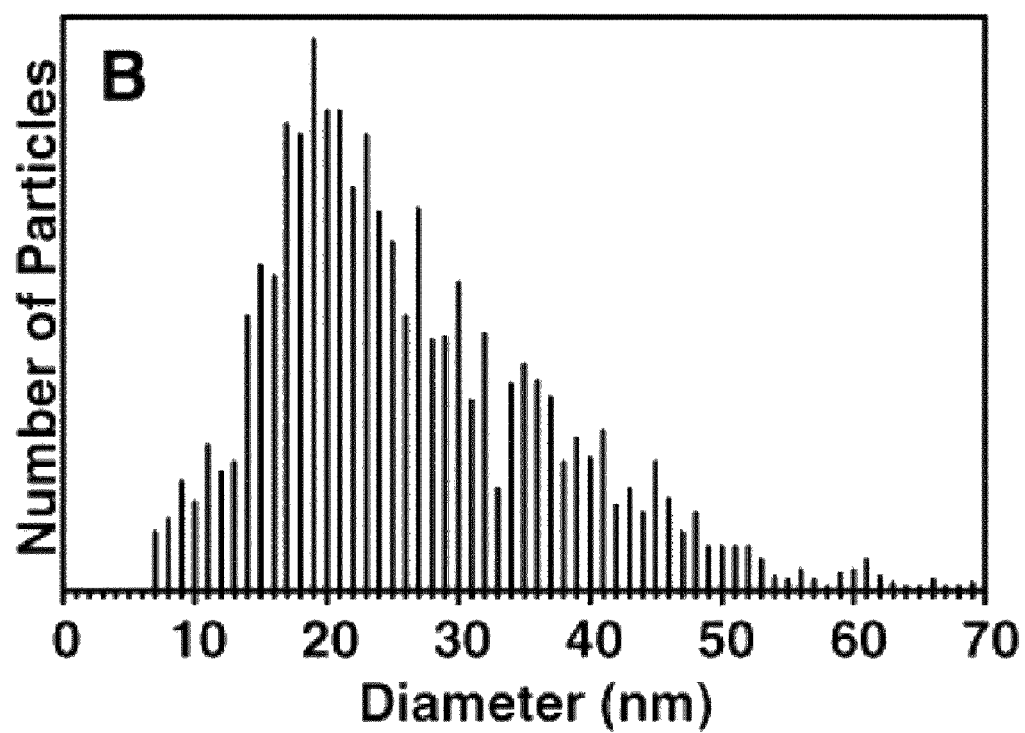
FIG. 3 is a histogram of the particle sizes obtained from TEM images of ~1400 $NaYF_4$: 2% $Er^{3+}$, 20% $Yb^{3+}$ nanocrystals.
Figure 4:
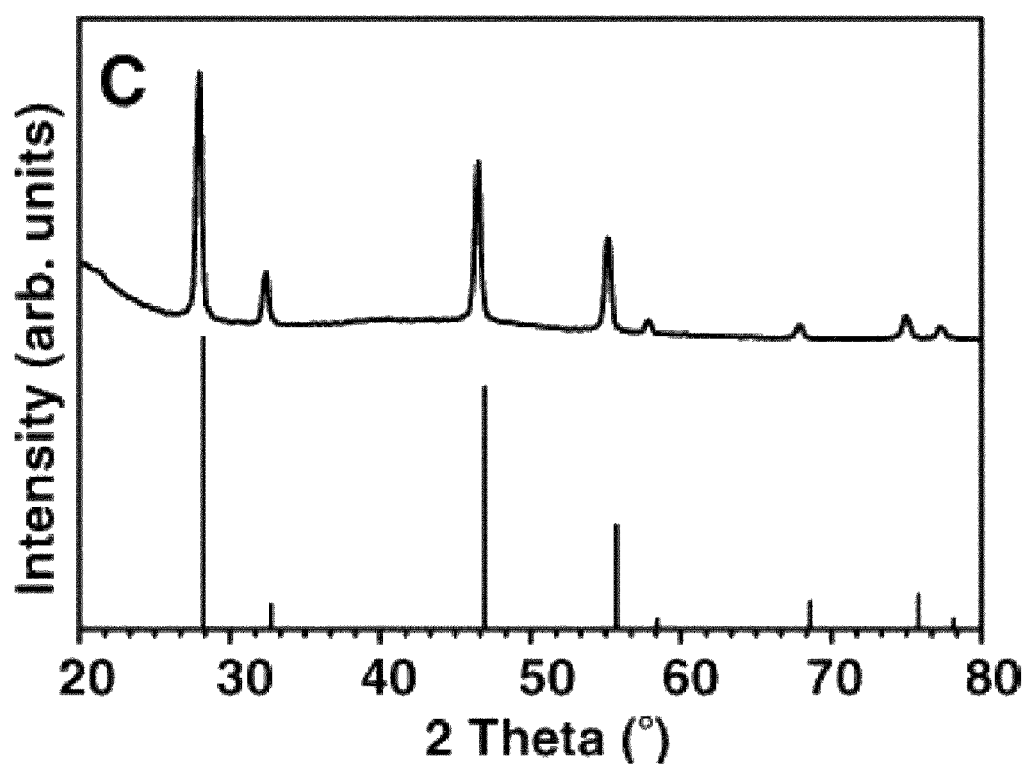
FIG. 4 is an experimental powder X-ray diffraction (XRD) pattern of $NaYF_4$: 2% $Er^{3+}$, 20% $Yb^{3+}$ (top curve) and the calculated line pattern for α-$NaYF_4$ (bottom curve)

FIGS. 2, 3 and 4 show the characterization data for a NaYF$_4$: 2% Er$^{3+}$, 20% Yb$^{3+}$ sample. The transmission electron microscopy (TEM) images (FIG. 2) show that the synthesized particles are roughly spherical. From the particle size distribution (FIG. 3), one can observe that the particles vary in size from 10 to 50 nm, with the majority falling in the range between 15 and 30 nm. The powder X-ray diffraction (XRD) pattern (FIG. 4) of the sample shows well-defined peaks, indicating the high crystallinity of the synthesized material. The peak positions and intensities from the experimental XRD pattern match closely with the calculated pattern for cubic α-NaYF$_4$ (Roy, D. M.; Roy, R. J. Electrochem. Soc. 1964, 111, 421-429). From the line broadening of the diffraction peaks, the crystallite size of the sample was determined to be approximately 25 nm using the Debye-Scherrer formula, which corresponds well to the average particle size determined from the TEM data.

Figure 5:
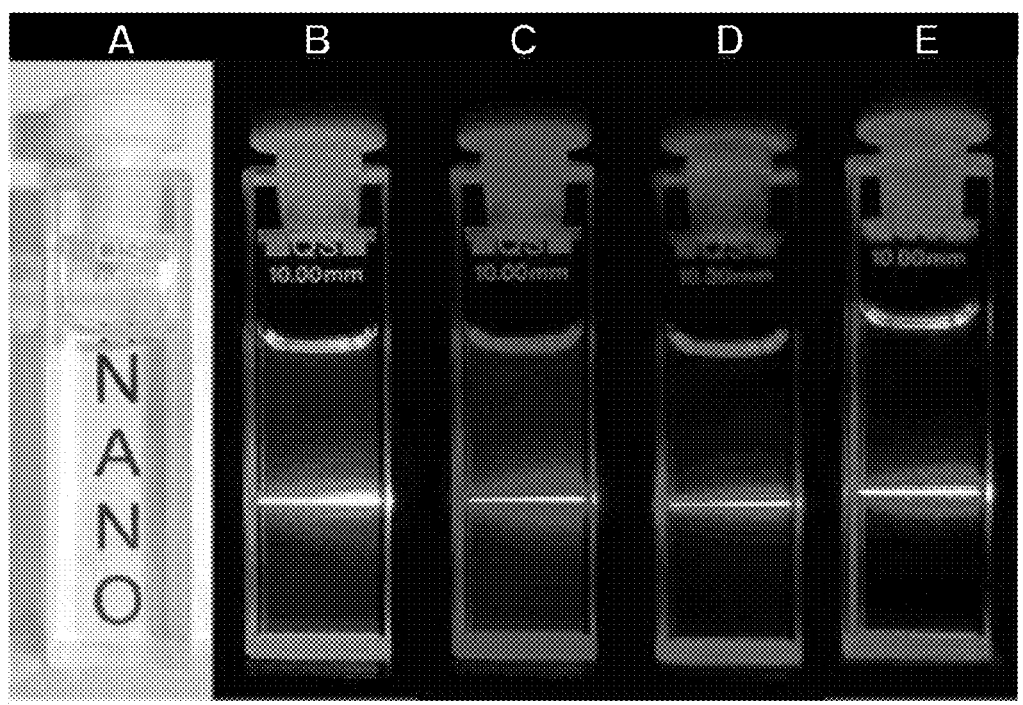
FIG. 5 shows 1 wt % colloidal solutions of nanocrystals in dichloromethane excited at 977 nm demonstrating upconversion luminescence, (A) $NaYF_4$: 2% $Er^{3+}$, 20% $Yb^{3+}$ solution showing its transparency, (B) total upconversion luminescence of $NaYF_4$: 2% $Er^{3+}$, 20% $Yb^{3+}$ solution, (C and D) $NaYF_4$: 2% $Er^{3+}$, 20% $Yb^{3+}$ upconversion viewed through green and red filters, respectively, and (E) total upconversion luminescence of $NaYF_4$: 2% $Tm^{3+}$, 20% $Yb^{3+}$.

FIG. 5A-D shows photographs of a 1 wt % solution of NaYF$_4$: 2% Er$^{3+}$, 20% Yb$^{3+}$ nanocrystals in dichloromethane, demonstrating its transparency (FIG. 5A) and the total visible upconversion luminescence under 977 nm excitation with a power density of 1.3 kW/cm$^2$ (FIG. 5B). FIGS. 5C and D shows the same solution through appropriate green and red filters, respectively. FIG. 5E demonstrates the upconversion luminescence of a 1 wt % solution of NaYF$_4$: 2% Tm$^{3+}$, 20% Yb$^{3+}$ in dichloromethane under the above excitation conditions.

Figure 6:
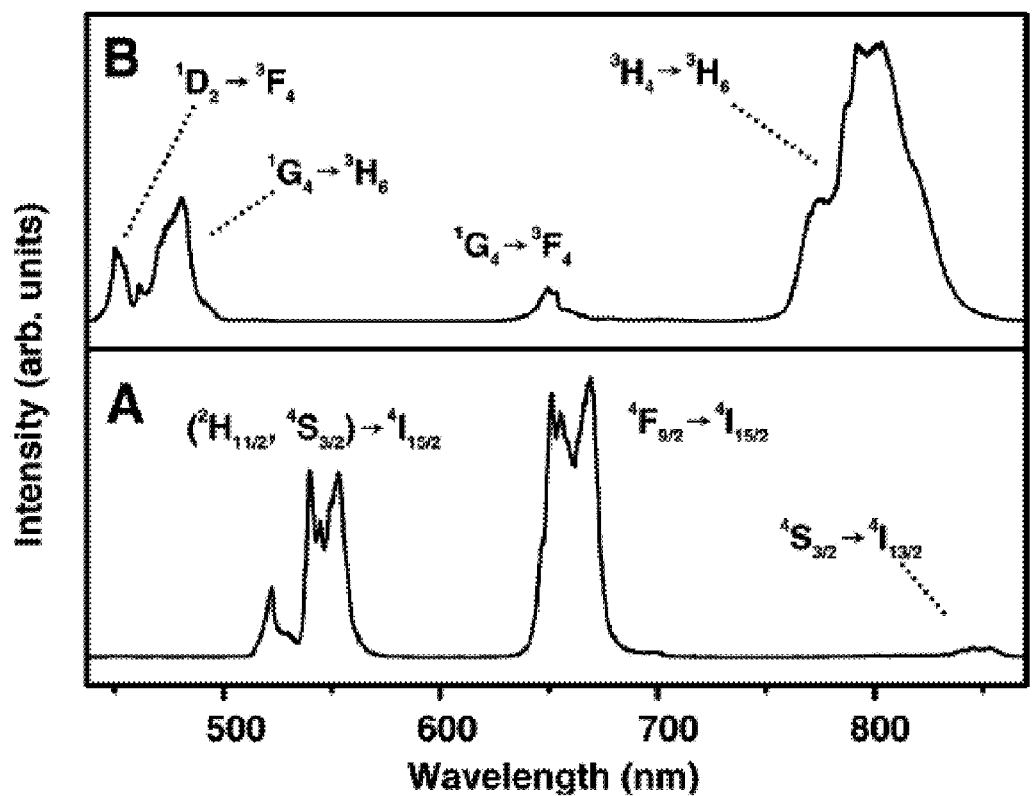
FIG. 6 is a luminescence emission spectra of 1 wt % colloidal solutions of nanocrystals in dichloromethane excited at 977 nm, (A) $NaYF_4$: 2% $Er^{3+}$, 20% $Yb^{3+}$ and (B) $NaYF_4$: 2% $Tm^{3+}$, 20% $Yb^{3+}$.
Figure 7:
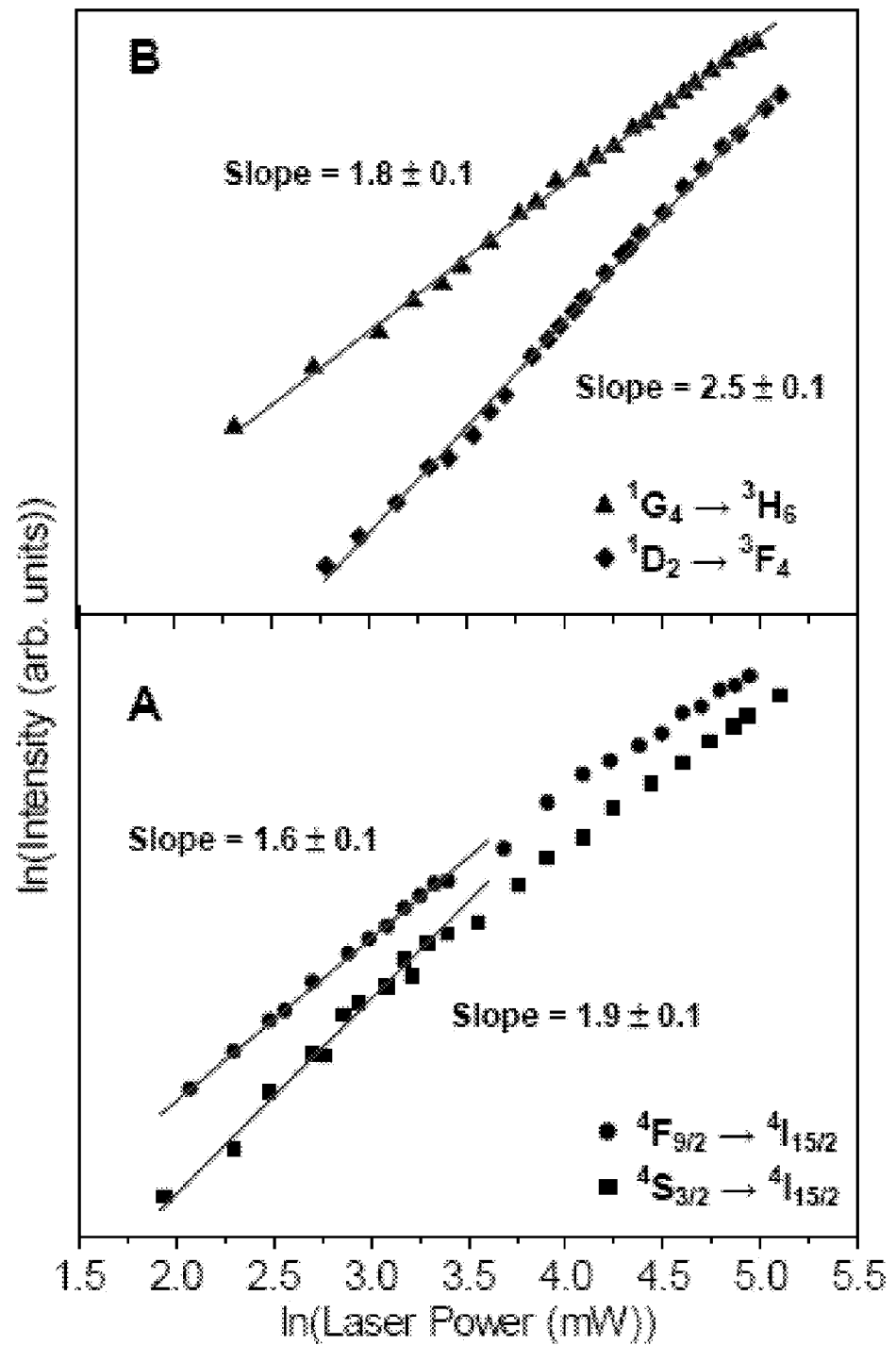
FIG. 7 is a power dependence of the upconverted emissions of 1 wt % colloidal solutions of nanocrystals in dichloromethane excited at 977 nm, (A) $NaYF_4$: 2% $Er^{3+}$, 20% $Yb^{3+}$ and B) $NaYF_4$: 2% $Tm^{3+}$, 20% $Yb^{3+}$ [In the case of the $NaYF_4$: 2% $Er^{3+}$, 20% $Yb^{3+}$ sample, the straight lines are least-squares fit to the low power data points. At higher excitation densities the power dependence of the emissions are observed to level off due to saturation of the upconversion processes. For the $NaYF_4$: 2% $Tm^{3+}$, 20% $Yb^{3+}$ sample, the least-squares fit to the data points give a value that is lower than the expected due to the saturation of the upconversion processes]
Figure 8:
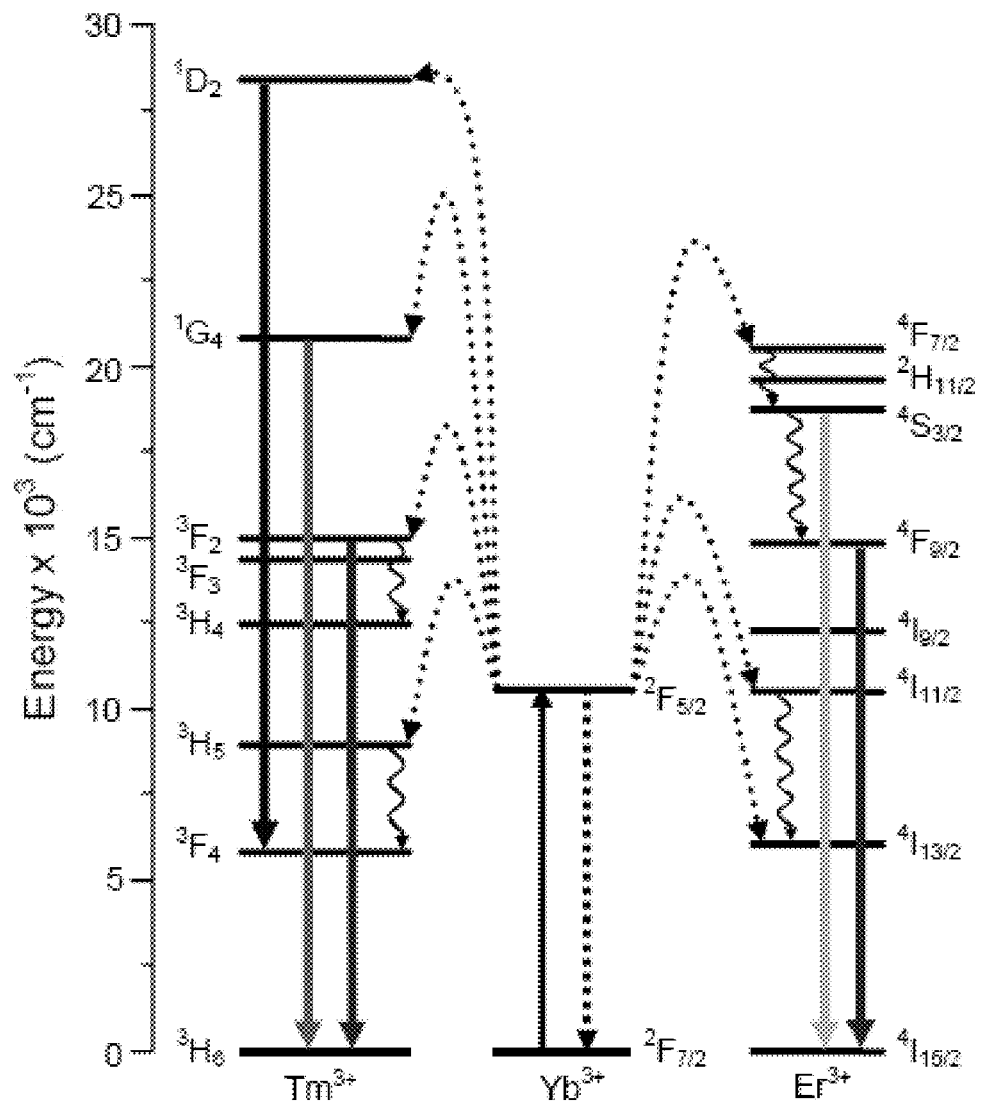
FIG. 8 shows energy level diagrams of the $Er^{3+}$, $Tm^{3+}$, and $Yb^{3+}$ dopant ions and upconversion mechanisms following 980 nm laser diode excitation [The full, dotted, and curly arrows represent emission, energy transfer, and multiphonon relaxation processes, respectively.]

The visible and NIR upconversion spectra of 1 wt % solutions of NaYF$_4$: 2% Er$^{3+}$, 20% Yb$^{3+}$ and NaYF$_4$: 2% Tm$^{3+}$, 20% Yb$^{3+}$ nanocrystals in dichloromethane under 977 nm excitation are shown in FIGS. 6A and B, respectively. The spectra correspond to what has been reported previously for Er$^{3+}$ and Tm$^{3+}$ upconversion in cubic NaYF$_4$ nanocrystals (Heer et al. Adv. Mater. 2004, 16, 2102-2105; Zeng et al. Adv. Mater. 2005, 17, 2119-2123; Wang et al. Angew. Chem., Int. Ed. 2005, 44, 6054-6057; Aebischer et al. Chem. Phys. Lett. 2005, 407, 124-128; and Suyver et al. Opt. Mater. 2005, 27, 1111-1130.). In the Er$^{3+}$ sample, green luminescence was observed from the ($^2$H$_{11/2}$, $^4$S$_{3/2}$)→$^4$I$_{15/2}$ and red from the $^4$F$_{9/2}$→$^4$I$_{15/2}$ transitions, respectively. The power dependencies of the green and red luminescence (FIG. 7) were found to be approximately 2, indicating that two photons were involved in the upconversion mechanism. Four spectral bands were observed in the Tm$^{3+}$ sample and were assigned to the $^1$G$_4$→$^3$H$_6$, $^1$D$_2$→$^3$F$_4$, $^1$G$_4$→$^3$F$_4$ and $^3$H$_4$→$^3$H$_6$ transitions. The mechanisms responsible for the upconversion luminescence are shown in FIG. 8.

The straightforward synthesis used here for preparing upconverting lanthanide-doped nanocrystals required few preparatory steps. The Er$^{3+}$, Yb$^{3+}$ and Tm$^{3+}$, Yb$^{3+}$ doped particles exhibited green/red and blue upconversion luminescence, respectively, under 977 nm laser excitation with low power densities.

Example 1

The synthesis, characterization, and spectroscopy of upconverting lanthanide-doped NaYF$_4$ nanocrystals (nanocrystals) is presented. Cubic NaYF$_4$ nanocrystals were synthesized via a thermal decomposition reaction of trifluoroacetate precursors in a mixture of technical-grade chemicals; octadecene and the coordinating ligand oleic acid. In this method, the dissolved precursors are added slowly to the reaction solution through a stainless-steel canula, resulting in highly luminescent nanocrystals with an almost monodisperse particle size distribution.

The nanocrystals were characterized through the use of transmission electron microscopy (TEM), selected area electron diffraction (SAED), $^1$H NMR, powder X-ray diffraction (XRD), and high-resolution luminescence spectroscopy. The NaYF$_4$ nanocrystals are capable of being dispersed in nonpolar organic solvents, thus forming colloidally stable solutions. The colloids of the Er$^{3+}$, Yb$^{3+}$- and Tm$^{3+}$, Yb$^{3+}$-doped nanocrystals exhibit green/red and blue upconversion luminescence, respectively, under 980 nm laser diode excitation with low power densities.

The method used here is a modification of the synthetic procedure of Comparative Example 1 and, in contrast with that method, resulted in the synthesis of cubic NaYF$_4$ particles with a narrow particle size range and well-defined shape. These particles are capable of being colloidally dispersed in various nonpolar organic solvents (e.g., hexane, toluene, dichloromethane) and are able to emit visible light under 980 nm laser diode excitation via the upconversion process under relatively low excitation power densities. Furthermore, this method uses inexpensive technical-grade chemicals, which reduces the cost of the nanoparticle synthesis and a relatively low-cost laser diode for excitation, hence making them attractive for potential commercial applications.

The lanthanide trifluoroacetate precursors for the synthesis were prepared from the corresponding lanthanide oxides and trifluoroacetic acid in a three-neck round-bottom flask. The corresponding amount of sodium trifluoroacetate was then added to the lanthanide trifluoroacetates in the reaction vessel with 5 mL of octadecene and 10 mL of oleic acid. A second solution of 15 mL of octadecene and 10 mL of oleic acid was then prepared in a second three-neck round-bottom flask. Both solutions were heated slowly to 125° C. under vacuum with stirring and kept at this temperature for 30 min to remove residual water and oxygen. The second solution was then heated to 310° C. under argon and maintained at this temperature. The lanthanide trifluoroacetate solution at 125° C. was then transferred dropwise into the second solution over a period of 15 min using a stainless-steel cannula at a flow rate of ca. 1 mL/min. During this time, the second solution was maintained at 310° C. After the addition was complete, the temperature of the reaction mixture was lowered to 305° C. and kept at this temperature for 1 h under dry argon. Subsequently, the mixture was removed from the heating mantle and cooled to room temperature. The nanocrystals were precipitated by the addition of excess ethanol and isolated via centrifugation. The resulting pellet was then washed twice by dispersing with ethanol and centrifugated. The resulting nanocrystals were dried under air for 24 h. Due to the presence of the capping ligand, the nanocrystals could be dispersed in nonpolar solvents and were colloidally stable in solution for a period of weeks with no visible agglomeration or settling.

A more detailed description of the synthetic procedure and spectroscopy setup is given below.

Synthesis of $Ln^{3+}$ doped $NaYF_4$ nanocrystals. All chemicals utilized in the synthesis of the nanocrystals were purchased from Aldrich. The lanthanide trifluoracetate precursors were prepared from the corresponding lanthanide and yttrium oxides and trifluoroacetic acid (99%). All oxides utilized were 99.99% purity or higher.

In the case of the $NaYF_4$: $Er^{3+}$ 2 mol %, $Yb^{3+}$ 20 mol % codoped sample, 9.6 mg (0.025 mmol) of $Er_2O_3$, 98.5 mg (0.25 mmol) of $Yb_2O_3$, and 220.2 mg (0.975 mmol) of $Y_2O_3$ were dissolved in 10 mL of 50% aqueous trifluoroacetic acid at 80° C. in a three-neck round-bottom flask. The residual water and acid were then slowly evaporated to dryness at 60° C. Sodium trifluoroacetate (98%) in the amount of 0.3400 g (2.5 mmol) was then added to the reaction vessel with 5 mL of octadecene (90%) and 10 mL of oleic acid (90%). A second solution of 15 mL of octadecene and 10 mL oleic acid was then prepared in a 100 mL three-neck round bottom flask. Both solutions were slowly heated to 125° C. under vacuum with magnetic stirring for 30 minutes to remove residual water and oxygen during which time the flask was purged periodically with dry argon gas. At this point, both solutions were clear with a slight yellow color.

The second solution was then heated to 310° C. under Ar and maintained at this temperature. The lanthanide trifluoroacetate solution at 125° C. was then transferred dropwise into the second solution over a period of 15 minutes using a stainless steel cannula at a flow rate of ca. 1 mL/min. During this time the second solution was maintained at 310° C. During the addition, the evolution of small gas bubbles was observed from the solution indicating the decomposition of the metal trifluoroacetates. Approximately 8-10 minutes into the addition of the trifluoroacetates, the reaction solution became turbid.

After the addition was complete, the reaction mixture was lowered to 305° C. and kept at this temperature for 1 hr under dry argon during which time the solution became clear and a yellow colloidal solution was obtained. Subsequently, the mixture was allowed to cool to room temperature at which point the solution became turbid once again.

The nanocrystals were precipitated by the addition of ethanol and isolated via centrifugation at 2000 rpm corresponding to a relative centrifugal field (RCF) of approximately 1000. The resulting pellet was then washed twice with ethanol and isolated via centrifugation at 2000 rpm each time. The resulting nanocrystals were dried in air for a minimum of 24 hrs.

The resulting nanocrystals could be dispersed in nonpolar solvents (e.g. hexane, toluene, dichloromethane) by sonicating a suspension of the nanocrystals in a bath sonicator for 10-20 minutes. To aid in the dispersion of the nanocrystals, it was preferable to leave them in a "muddy" state instead of the dry powder form.

NMR Measurements. The $^1H$ NMR spectrum of an undoped NaYF4 sample dispersed in $CDCl_3$ was recorded using a Varian 300 MHz spectrometer. The spectrometer frequency was 300.03 MHz and 128 transients were recorded. The residual proton signal of the deuterated solvent was used as internal standards ($CDCl_3$ $^1H$ δ: 7.27 ppm). The $^1H$ NMR of free oleic acid was also obtained using the same experimental conditions for reference.

Powder X-ray Diffraction Analysis. The powder diffraction patterns were collected at room temperature with the Kα (40 kV, 20 mA) radiation of Cu on a PW-1050 Philips diffractometer automated with the Difftech Sie-Ray system. Data accumulation and processing were carried out using the Difftech Sie-122 software. The scanning step size was 0.05° 2θ with a counting time of 10 s per step.

Transmission Electron Microscopy (TEM) Studies. TEM was performed on a $NaYF_4$: $Er^{3+}$+2%, $Yb^{3+}$+20% sample using a JEOL JEM-2000 FX microscope operating at 80 kV equipped with a charged-coupled device (CCD)-camera (Gatan). A small amount of the sample (~1 mg) was dispersed in 1 g of hexane to give an approximate 0.1 wt % solution. One drop of the resulting solution was allowed evaporated on a formvar/carbon film supported on a 300 mesh copper grid (3 mm in diameter). High resolution TEM was performed on the same sample using a 200 KeV JEOL JEM-2100F microscope.

Visible and NIR Room Temperature Upconversion Emission Spectroscopy ($\lambda_{exc}$=980 nm). The upconverted emission spectra were obtained using a Coherent 6-pin fibre-coupled F6 series 980 nm laser diode with a maximum power of 800 mW at 1260 mA. The laser was coupled to a 100 μm (core) fibre. For the upconversion studies, the samples were placed in 1 cm path-length quartz cuvettes (Hellma, QS). The visible emissions were collected from the samples at π/2 from the incident beam and then dispersed by a 1 m Jarrell-Ash Czerny-Turner double monochromator. Resolution of the monochromator was 0.2 nm with slit widths of 200 μm. The visible emissions from the sample exiting the monochromator were detected by a thermoelectrically cooled Hamamatsu R943-02 photomultiplier tube and the photomultiplied signals were processed by a Stanford Research Systems (SRS) model SR440 preamplifier. A Stanford Research Systems model SR 400 gated photon counter data acquisition system was used as an interface between the spectroscopic equipment and the computer running the SRS SR 465 data acquisition software.

Figure 9:
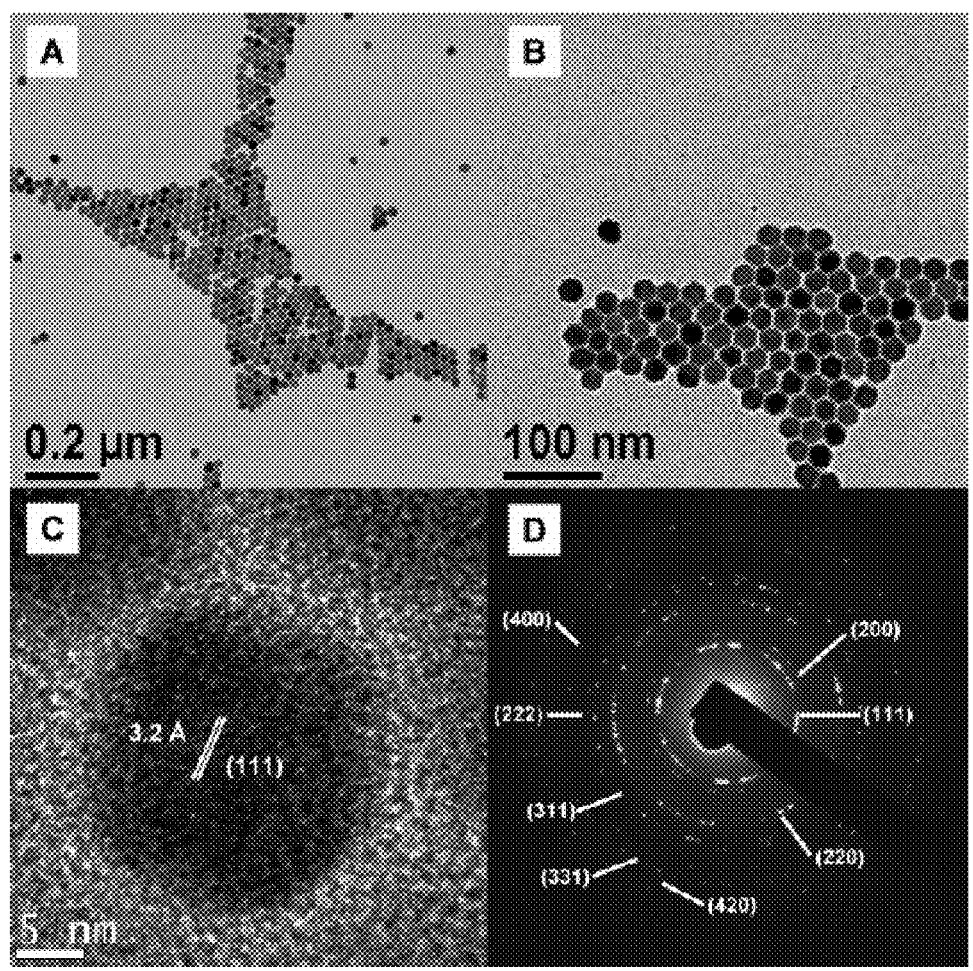
FIGS. 9 (A and B) is a low-resolution transmission electron micrographs of a $NaYF_4$: 2% $Er^{3+}$, 20% $Yb^{3+}$ sample showing uniformity of the particles, (C) is a high-resolution micrograph of a single $NaYF_4$: 2% $Er^{3+}$, 20% $Yb^{3+}$ particle showing lattice fringes, and (D) is a selected area electron diffraction pattern (SAED) of $NaYF_4$: 2% $Er^{3+}$, 20% $Yb^{3+}$ particles.
Figure 10:
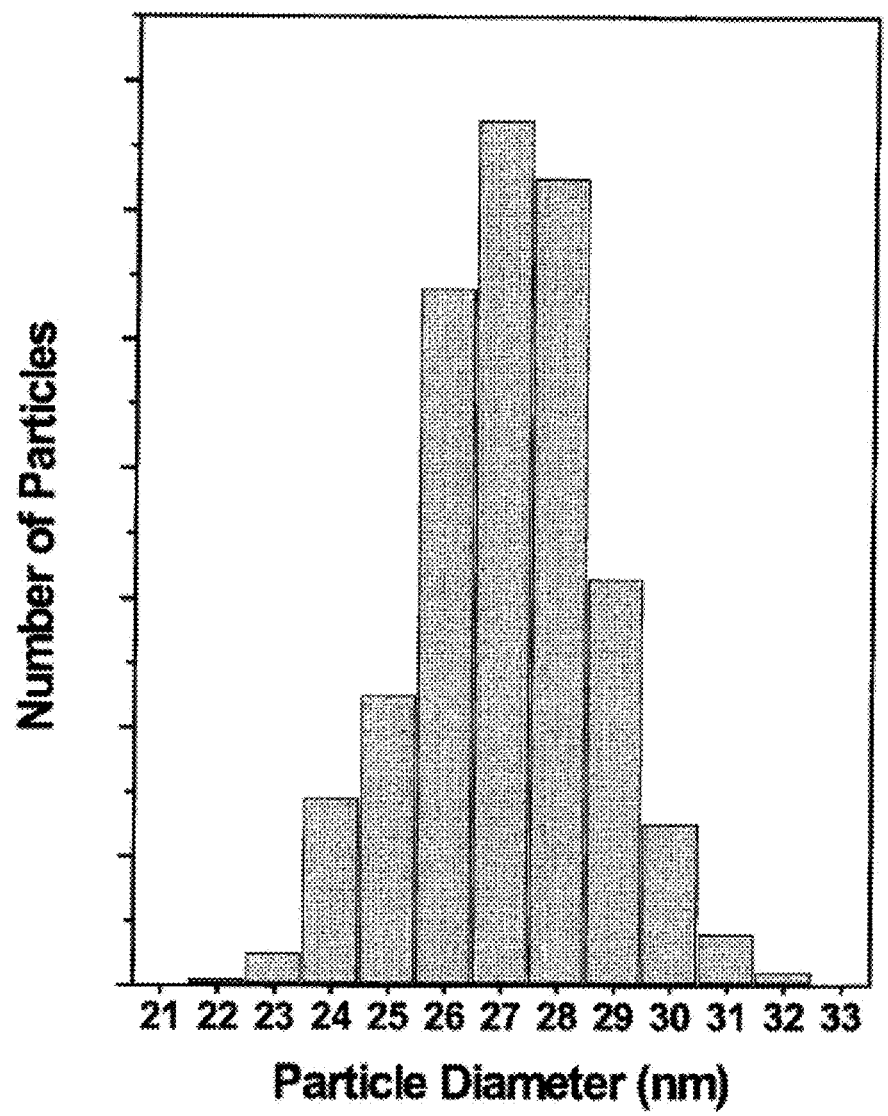
FIG. 10 is a histogram of the particle sized obtained from TEM images of ~500 $NaYF_4$: 2% $Er^{3+}$, 20 $Yb^{3+}$ nanocrystals [average particle size=27.6±1.6 nm.]

FIG. 9 shows the transmission electron microscopy (TEM) data for a $NaYF_4$: 2% $Er^{3+}$, 20% $Yb^{3+}$ nanocrystals sample. From the low-resolution micrographs, FIGS. 9A and B, one can observe that the synthesized particles appear hexagonal in shape and are nearly monodisperse. From a detailed particle size analysis of 500 particles from several low-resolution TEM micrographs (FIG. 10), the average particle size was found to be 27.6 nm with a standard deviation of 1.6 nm. Further proof of the uniform particle size and shape of the particles reported herein is provided by their assembly into a regular two-dimensional hexagonal close packed arrangement on the TEM grid due to the presence of the oleic acid capping ligand on the surface of the particles.

From the high-resolution TEM (HRTEM) image, FIG. 9C, the distance between the particles was found to be 2.8±0.5 nm, which is somewhat less than two times the length of a single oleate molecule (2.2 nm from semiempirical calculation). This is a good indication that there is interdigitation of the alkyl chains from neighboring particles or that the oleic acid chains are not in a fully extended conformation.

From the HRTEM image, one can also clearly distinguish lattice fringes on the individual particles indicating that the particles are highly crystalline. The distances between the lattice fringes were measured to be 3.2 and 2.8, which correspond to the d spacing for the (111) and (200) lattice planes, respectively, in the cubic $NaYF_4$ structure (Pol et al. Indian J. Pure Appl. Phys. 1973, 11, 886-8; Reddy et al. J. Mater. Sci. Lett. 1983, 2, 83-84; and Roy et al. J. Electrochem. Soc. 1964, 111, 421-429). From this, we can conclude that the particles have a polyhedron shape and are truncated octahedrons bordered by the (111) and (002) lattice planes (Wang, J. Phys. Chem. B 2000, 104, 1153-1175). The hexagonal shape of the particles observed in the TEM images are 2D projections of the 3D truncated octahedral geometry. The selected area electron diffraction (SAED) pattern of the particles (FIG. 9D) can be indexed to the (111), (200), (220), (311), (222), (400), and (331) planes of the standard cubic α-$NaYF_4$ structure (JCPDS: 6-0342) as seen in Table 1. In addition, the particles were found to be single crystallites because the Fourier transformation on individual particles returned patterns corresponding to a single set of (111) and (200) planes.

TABLE 1 d-spacing values $NaYF_4$: 2% $Er^{3+}$, 20% $Yb^{3+}$; $NaYF_4$: 2% $Tm^{3+}$, 20% $Yb^{3+}$; and $NaYF_4$ as determined via Electron Diffraction (ED) and X-ray Diffraction (XRD).

| | d-spacing values (Å) | | | | |
|---|---|---|---|---|---|
| h k l | $NaYF_4$: 2% $Er^{3+}$, 20% $Yb^{3+}$ (ED) | $NaYF_4$: 2% $Er^{3+}$, 20% $Yb^{3+}$ (XRD) | $NaYF_4$: 2% $Tm^{3+}$, 20% $Yb^{3+}$ (XRD) | $NaYF_4$ (XRD) | Standard pattern (JCPDS: 6-0342) |
| 1 1 1 | 3.15 | 3.19 | 3.19 | 3.19 | 3.14 |
| 2 0 0 | 2.72 | 2.76 | 2.76 | 2.76 | 2.73 |
| 2 2 0 | 1.92 | 1.95 | 1.95 | 1.95 | 1.93 |
| 3 1 1 | 1.64 | 1.66 | 1.66 | 1.66 | 1.64 |
| 2 2 2 | 1.57 | 1.59 | 1.59 | 1.59 | 1.57 |
| 4 0 0 | 1.36 | 1.38 | 1.38 | 1.38 | 1.36 |
| 3 3 1 | 1.26 | 1.27 | 1.27 | 1.26 | 1.25 |
| 4 2 0 | 1.22 | 1.23 | 1.23 | 1.23 | 1.22 |

In Comparative Example 1, the synthesis of α-$NaYF_4$ nanoparticles in octadecene and oleic acid resulted in irregularly shaped particles with a wide particle size range. It is clear from the TEM data that the modifications made to the earlier synthetic procedure unexpectedly results in α-$NaYF_4$ nanoparticles with defined shapes and monodisperse size distributions. Without, being bound by theory, it is believed that the decomposition of the trifluoroacetate precursors and thus the crystallization of the $NaYF_4$ particles occur quite fast at the temperatures used in this synthesis (310° C.). By adding the precursors to the solution slowly, the inventors found that one can control the rate of decomposition and formation of the particles. In essence, by performing the addition over a longer period of time, one can separate the nucleation and growth phases of the nanocrystals resulting in a monodisperse particle size. The inventors also found that this method also allows the oleic acid to complex to the surface of the growing particles more effectively due to the initial low concentration of precursor in the solution. The oleic acid ligands thus modulate the growth rate along the (111) and (200) directions of the cubic NaYF4 nanocrystals, resulting in the truncated octahedral shape.

Figure 11:
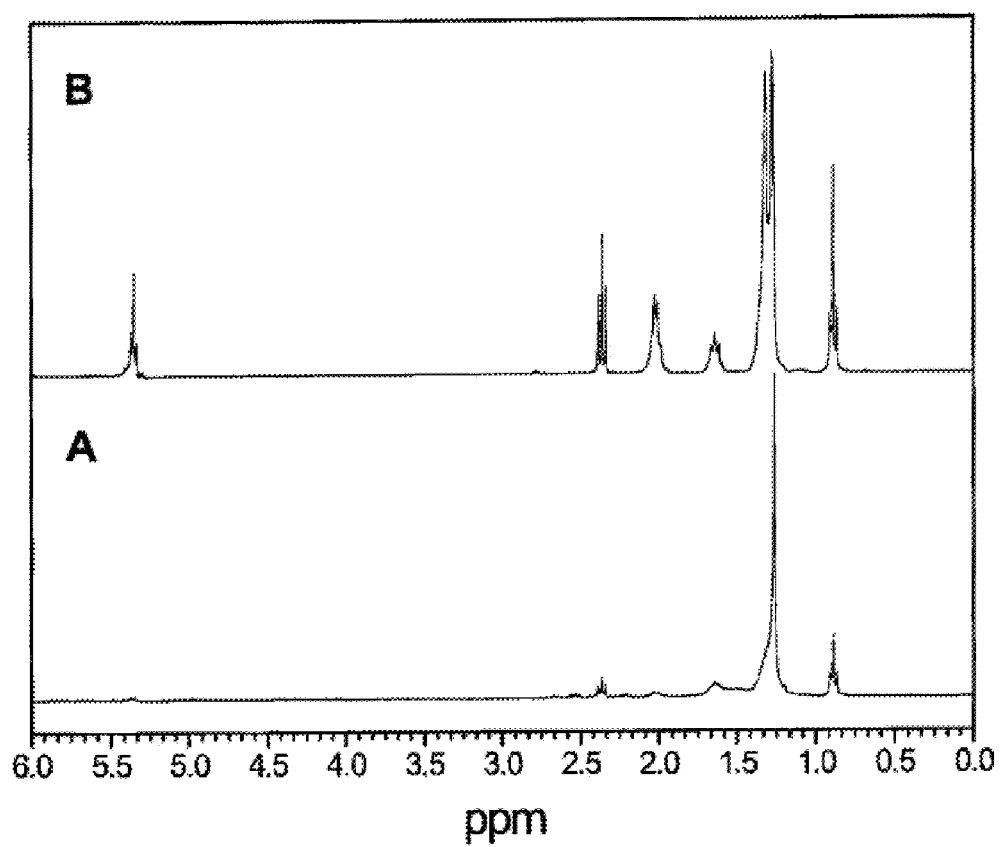
FIG. 11 is a $^1$H NMR spectra of (A) an undoped $NaYF_4$ sample and (B) free oleic acid in $CDCl_3$ recorded on a Varian 300 MHz spectrometer [Chemical shifts for $NaYF_4$ sample are reported in parts-per-million δ: 5.3-5.45 (broad, —HC═CH—), 2.3-2.4 (broad, —$CH_2$—COOH), 2.0-2.1 (broad, $CH_3$—$(CH_2)_6$—$CH_2$—CH═CH—$CH_2$—$(CH_2)_6$—COOH), 1.2-1.4 (broad, —$(CH_2)_6$—) and 0.85-1.00 (broad, —$CH_3$).]

The presence of the oleic acid ligand on the surface of the nanocrystals was confirmed using $^1H$ NMR of an undoped $NaYF_4$ sample. The $^1H$ NMR of the undoped $NaYF_4$ sample dispersed in $CDCl_3$ is shown in FIG. 11, along with the $^1H$ NMR of free oleic acid for reference. The $^1H$ NMR signals of the bound oleic acid molecules on the surface of the nanoparticles are broadened with respect to those of the free oleic acid. The broadening is due to an inhomogeneous distribution of the magnetic environments due to site variations on the nanoparticle surface as well as a decrease in the rotational freedom of the oleic acid ligands (Sudarsan et al. Chem. Mater. 2005, 17 (18), 4736-4742; Sachleben et al. Chem. Phys. Lett. 1992, 198 (5), 431-436; and Kuno et al. J. Chem. Phys. 1997, 23, 9869-9882).

Figure 12:
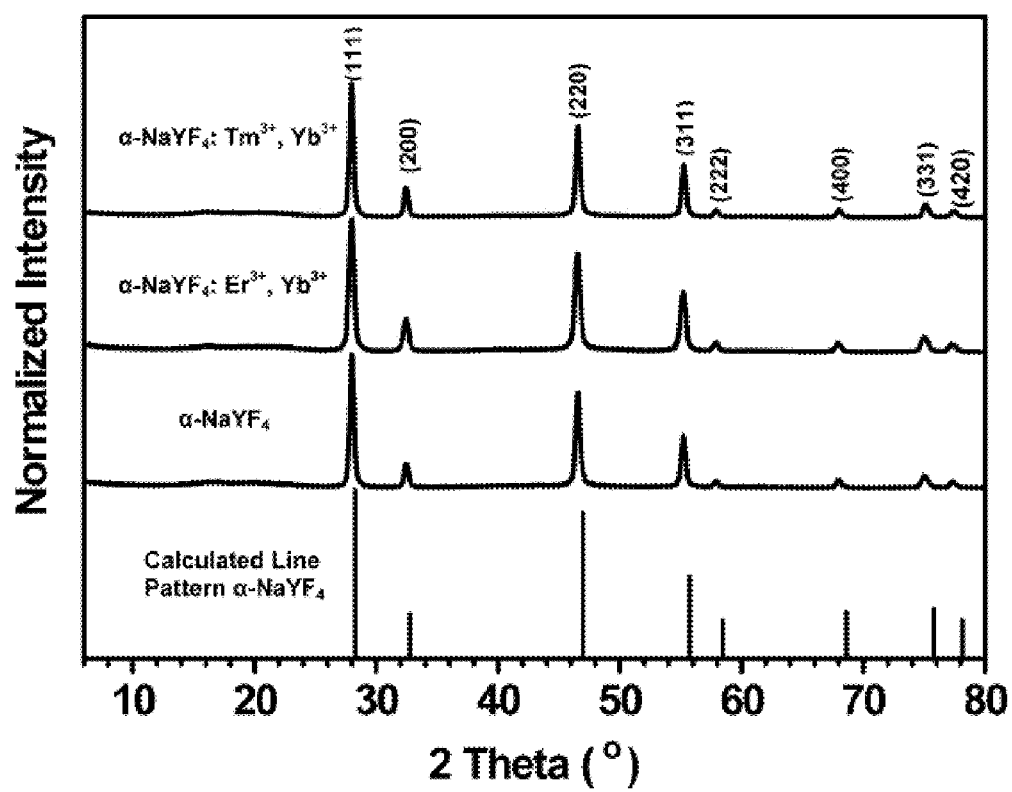
FIG. 12 is an experimental powder X-ray diffraction (XRD) patterns of α-$NaYF_4$, α-$NaYF_4$: 2% $Er^{3+}$, 20% $Yb^{3+}$, and α-$NaYF_4$: 2% $Tm^{3+}$, 20% $Yb^{3+}$ nanocrystals [The calculated line pattern for α-$NaYF4$ (bottom plot) is shown for reference.]

FIG. 12 shows the powder X-ray diffraction (XRD) patterns for the $NaYF_4$: 2% $Er^{3+}$, 20% $Yb^{3+}$; $NaYF_4$: 2% $Tm^{3+}$, 20% $Yb^{3+}$ and $NaYF_4$ nanocrystals as well as the calculated line pattern for α-NaYF4. It is evident from the intensity of the peaks in the obtained patterns that the materials in question are highly crystalline in nature. The peak positions of all three patterns correspond closely to the reported and calculated patterns for cubic α-NaYF4 (Pol et al. Indian J. Pure Appl. Phys. 1973, 11, 886-8; Reddy et al. J. Mater. Sci. Lett. 1983, 2, 83-84; and Roy et al. J. Electrochem. Soc. 1964, 111, 421-429). The calculated d-spacing values for all three samples and the corresponding h k l values are given in Table 1. These values obtained from the nanocrystalline samples closely match the standard pattern of α-NaYF4 (JCPDS: 6-0342), and no peaks from other phases or impurities were observed.

The lattice constants for the $NaYF_4$: 2% $Er^{3+}$, 20% $Yb^{3+}$; $NaYF_4$: 2% $Tm^{3+}$, 20% $Yb^{3+}$ and $NaYF_4$ nanocrystals were calculated to be 5.519, 5.515, and 5.517 Å, respectively, which correspond closely to previously reported lattice constants of 5.485 and 5.47 Å for nanocrystalline (Heer et al. Adv. Mater. 2004, 16, 2102-2105) and bulk (Roy et al. J. Electrochem. Soc. 1964, 111, 421-429) α-$NaYF_4$. The broad nature of the observed diffraction peaks is an indication of the small size of the nanocrystals. From the line broadening of the (111) diffraction peak of the $NaYF_4$: 2% $Er^{3+}$, 20% $Yb^{3+}$ sample, an average crystallite size of 25 nm was calculated using the Debye-Sherrer formula. This value matches closely to the particle size determined from the TEM results.

Figure 13:
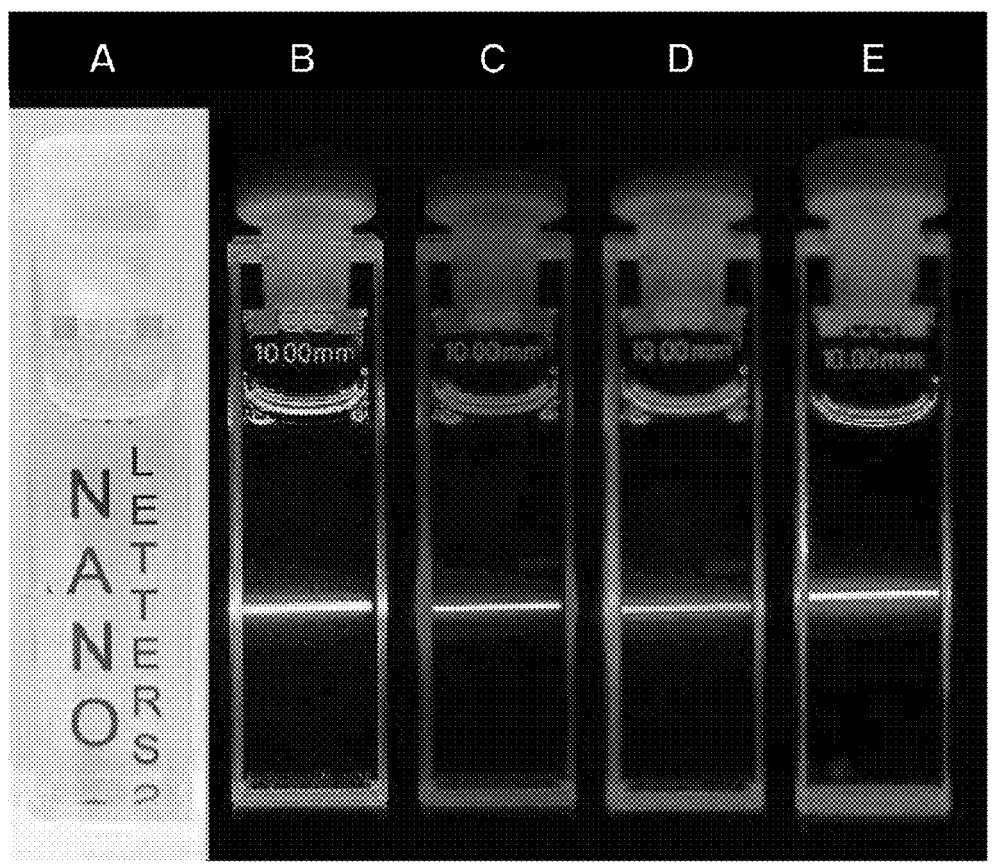
FIG. 13 shows colloidal solutions (1 wt %) of nanocrystals in toluene excited with a 980 nm laser diode (power density=100 W/cm$^2$) demonstrating upconversion luminescence, (A) NaYF$_4$: 2% Er$^{3+}$, 20% Yb$^{3+}$ solution showing its transparency, (B) total upconversion luminescence of NaYF$_4$: 2% Er$^{3+}$, 20% Yb$^{3+}$ solution, (C and D) NaYF$_4$: 2% Er$^{3+}$, 20% Yb$^{3+}$ upconversion viewed through green and red filters, respectively, and (E) total upconversion luminescence of NaYF$_4$: 2% Tm$^{3+}$, 20% Yb$^{3+}$ solution.

FIG. 13A-D shows photographs of a 1 wt % solution of $NaYF_4$: 2% $Er^{3+}$, 20% $Yb^{3+}$ nanocrystals in toluene. The transparency of the resulting colloidal solution is clearly demonstrated in the first image, FIG. 13A. FIG. 13B shows the total upconversion luminescence of the same solution under 980 nm laser diode excitation into the $^2F_{7/2} \rightarrow {}^2F_{5/2}$ absorption of the $Yb^{3+}$ ion with a power density of 100 W/cm$^2$. The total luminescence appears yellow-green in color due to a combination of green and red emissions from the $Er^{3+}$ ion. This is apparent in FIGS. 13C and D where the solution under the same excitation conditions is viewed through green and red filters, respectively, thus isolating the two separate emissions. FIG. 13E shows a 1 wt % solution of $NaYF_4$: 2% $Tm^{3+}$, 20% $Yb^{3+}$ nanocrystals in toluene under identical excitation conditions demonstrating a primarily blue luminescence in the visible region of the spectrum.

Figure 14:
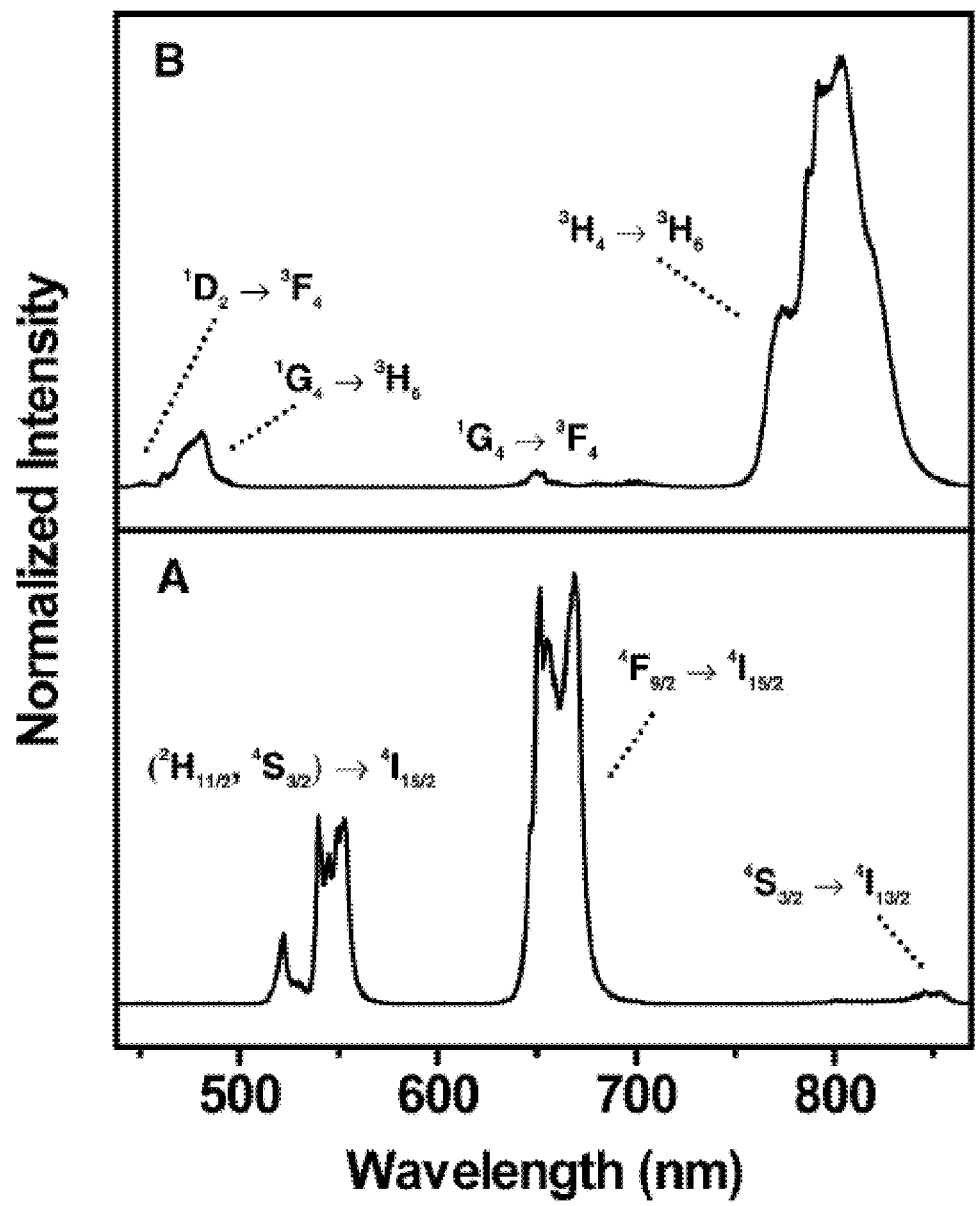
FIG. 14 is a luminescence emission spectra of 1 wt % colloidal solutions of nanocrystals in toluene excited with a 980 nm laser diode, (A) NaYF$_4$: 2% Er$^{3+}$, 20% Yb$^{3+}$ and (B) NaYF$_4$: 2% Tm$^{3+}$, 20% Yb$^{3+}$.

The upconversion spectra of both 1 wt % solutions of $NaYF_4$: 2% $Er^{3+}$, 20% $Yb^{3+}$ and $NaYF_4$: 2% $Tm^{3+}$, 20% $Yb^{3+}$ nanocrystals in toluene under 980 nm laser diode excitation (power density=100 W/cm$^2$) are shown in FIGS. 14A and B, respectively, and correspond to what has been reported previously for these materials (Heer et al. Adv. Mater. 2004, 16, 2102-2105) and that of Comparative Example 1. The emission bands can easily be assigned to transitions within the 4f-4f levels of the $Er^{3+}$ and $Tm^{3+}$ ions. The spectrum of the $NaYF_4$: 2% $Er^{3+}$, 20% $Yb^{3+}$ sample (FIG. 14A) exhibits three distinct $Er^{3+}$ emission bands. The green emissions between 510 and 530 nm and 530 and 570 nm were assigned to the $^2H_{11/2} \rightarrow ^4I_{15/2}$ and $^4S_{3/2} \rightarrow ^4I_{15/2}$ transitions, respectively. A dominant red emission was observed between 635 and 700 nm originating from the $^4F_{9/2} \rightarrow ^4I_{15/2}$ transition as well as a weak NIR emission between 830 and 860 nm corresponding to the $^4S_{3/2} \rightarrow ^4I_{13/2}$ transition. Four $Tm^{3+}$ emission bands were observed in the $NaYF_4$: 2% $Tm^{3+}$, 20% $Yb^{3+}$ sample (FIG. 14B) upon 980 nm laser diode excitation. The band observed in the blue region of the spectrum between 440 and 500 nm was assigned to the $^1D_2{}^3F_4$ and $^1G_4 \rightarrow ^3H_6$ transitions. A weak red emission between 630 and 670 nm and an intense NIR emission between 750 and 850 nm were assigned to the $^1G_4 \rightarrow ^3F_4$ and $^3H_4 \rightarrow ^3H_6$ transitions, respectively.

Figure 15:
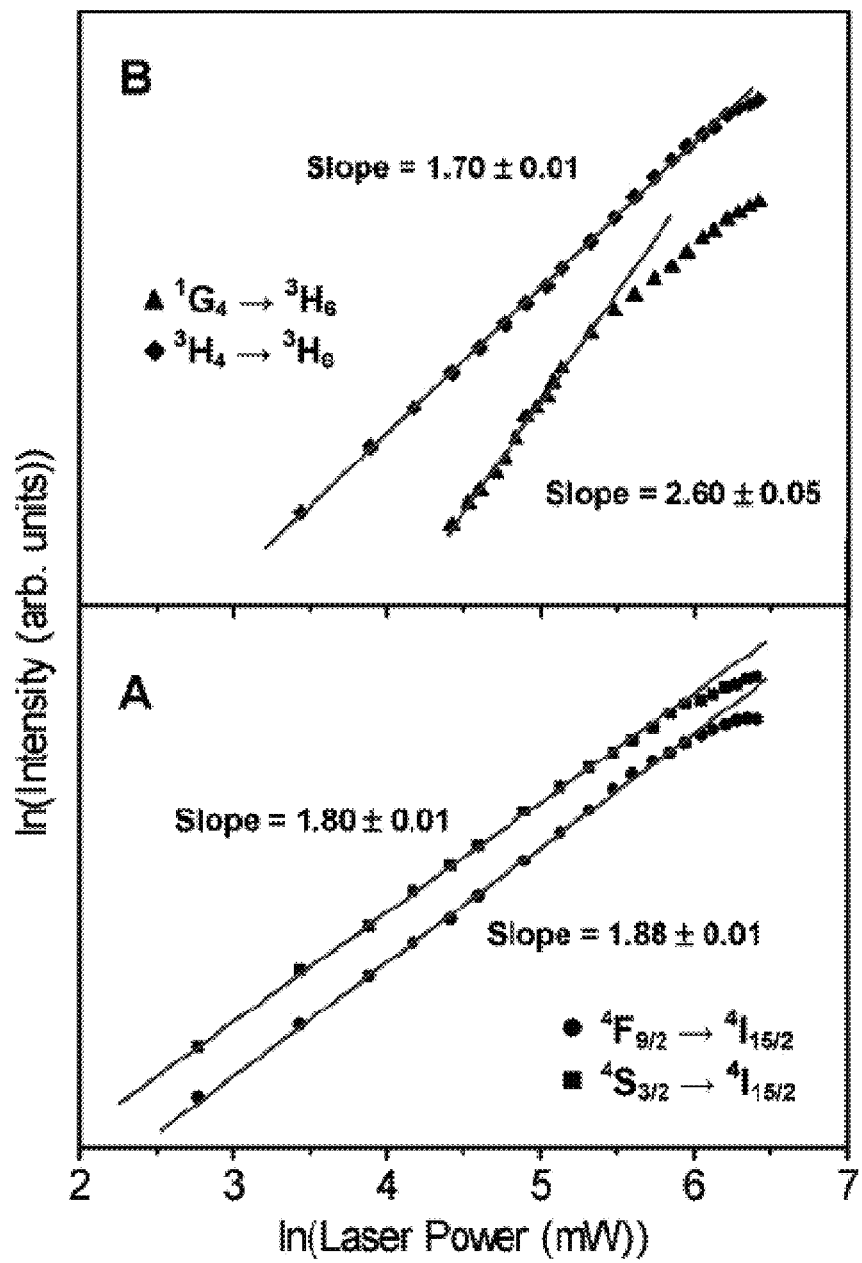
FIG. 15 shows the power dependence of the upconverted emissions of 1 wt % colloidal solutions of nanocrystals in toluene excited at 980 nm, (A) NaYF$_4$: 2% Er$^{3+}$, 20% Yb$^{3+}$ and (B) NaYF$_4$: 2% Tm$^{3+}$, 20% Yb$^{3+}$ [The straight lines are least-squares fits to the low power data points. At higher excitation densities, the power dependence of the emissions is observed to level off due to saturation of the upconversion processes.].

To determine the number of photons responsible for the upconversion mechanism, the intensities of the upconversion emissions as a function of the 980 nm excitation intensity were recorded (FIG. 15). As seen in FIG. 15A, the green and red $Er^{3+}$ upconversion emission intensities demonstrated quadratic power dependencies at low excitation densities indicating two photon upconversion mechanisms. For the $Tm^{3+}$ doped sample (FIG. 15B), three and two photon power dependencies were observed for the $^1G_4 \rightarrow ^3H_6$ and $^3H_4 \rightarrow ^3H_6$ emissions at low excitation densities, respectively. The power dependencies of the $Er^{3+}$ and $Tm^{3+}$ upconversion emissions became linear at high excitation densities due to "saturation" of the upconversion processes (Pollnau et al. Phys. Rev. B 2000, 61 (5), 3337-3346). Upconversion is a nonlinear process; as such it will not maintain its nonlinear behavior up to infinite excitation energies as a consequence of the conservation of energy. Hence, at high excitation densities the power dependence of the upconversion luminescence intensity will become linear, and a "saturation" of the luminescence intensity is observed.

The upconversion excitation pathways for the $Er^{3+}/Yb^{3+}$ and $Tm^{3+}/Yb^{3+}$ ion couples in these materials are well known ((Page et al. J. Opt. Soc. Am. B 1998, 15 (3), 996-1008) and are shown in FIG. 8. In the case of $NaYF_4$: 2% $Er^{3+}$, 20% $Yb^{3+}$, an initial energy transfer from an $Yb^{3+}$ ion in the $^2F_{5/2}$ state to an $Er^{3+}$ ion populates the $^4I_{11/2}$ level. A second 980 nm photon, or energy transfer from an $Yb^{3+}$ ion, can then populate the $^4F_{7/2}$ level of the $Er^{3+}$ ion. The $Er^{3+}$ ion can then relax nonradiatively (without emission of photons) to the $^2H_{11/2}$ and $^4S_{3/2}$ levels and the green $^2H_{11/2} \rightarrow ^4I_{15/2}$ and $^4S_{3/2} \rightarrow ^4I_{15/2}$ emissions occur. Alternatively, the ion can further relax and populate the $^4F_{9/2}$ level leading to the red $^4F_{9/2} \rightarrow ^4I_{15/2}$ emission. The $^4F_{9/2}$ level may also be populated from the $^4I_{13/2}$ level of the $Er^{3+}$ ion by absorption of a 980 nm photon, or energy transfer from an $Yb^{3+}$ ion, with the $^4I_{13/2}$ state being initially populated via the nonradiative $^4I_{11/2} \rightarrow ^4I_{13/2}$ relaxation. For the $NaYF_4$: 2% $Tm^{3+}$, 20% $Yb^{3+}$ sample, up to four subsequent energy transfers from $Yb^{3+}$ ions populate the upper $Tm^{3+}$ levels (FIG. 8) and various emissions can occur.

In summary, upconverting lanthanide-doped $NaYF_4$ nanocrystals (nanocrystals) have been prepared by thermal decomposition reaction of trifluoroacetate precursors in a mixture of octadecene and oleic acid. The nanocrystals produced by this method are ~28 nm in diameter on average with an almost monodisperse particle size distribution. SAED and powder XRD indicate that the nanocrystals are cubic α-$NaYF_4$. HRTEM shows that the nanocrystals are highly crystalline and are composed of single crystallites. The $Er^{3+}/Yb^{3+}$- and $Tm^{3+}/Yb^{3+}$-doped nanocrystals are capable of upconverting NIR light from a 980 nm diode laser into red/green and blue light, respectively.

The new synthetic method used here is highly attractive because it uses technical-grade solvents and ligands yet unexpectedly produces highly luminescent and uniform nanocrystals. The synthesis does not involve sophisticated equipment or complicated procedures, and the resulting nanocrystals are capable of being excited with a 980 nm laser diode thereby increasing their commercialization possibilities.

Although the present invention has been described hereinabove by way of specific embodiments thereof, it can be modified, without departing from the spirit and nature of the subject invention as defined in the appended claims.

The invention claimed is:

1. Lanthanide-doped uniformly shaped cubic $NaYF_4$ nanocrystals having an average particle size of at most about 50 nm with a standard deviation of at most about 15%, wherein, when observed by Transmission Electron Microscopy (TEM), said nanocrystals appear arranged into a regular two-dimensional hexagonal close packed arrangement.

2. A method of preparing lanthanide-doped cubic $NaYF_4$ nanocrystals as defined in claim 1, the method comprising:
   (a) providing a first solution comprising a non-coordinating solvent, a fatty acid coordinating ligand, sodium trifluoroacetate, yttrium trifluoroacetate, a first doping lanthanide trifluoroacetate and a second doping lanthanide trifluoroacetate, and a second solution comprising said non-coordinating solvent and said fatty acid coordinating ligand, said first and second solutions being substantially free of water and oxygen;
   (b) in an inert atmosphere, slowly adding the first solution heated at a temperature between about 100° C. and about 150° C. to the second solution heated at temperature between about 290° C. and about 330° C., thereby producing a reaction mixture containing said nanocrystals;
   (c) recovering said nanocrystals from said reaction mixture.

3. The method of claim 2 wherein said first and second doping lanthanides are erbium and ytterbium, or thulium and ytterbium.

4. The method of claim 2 further comprising maintaining the reaction mixture at a temperature between about 290° C. and about 330° C. under said inert atmosphere before (c).

5. The method of claim 4 wherein said maintaining step lasts at least about 1 hour.

6. The method of claim 2 wherein said first solution is added to said second solution in a small substantially steady stream.

7. The method of claim 2 wherein said first solution is added to said second solution through a cannula.

8. The method of claim 2 wherein said first solution is added to said second solution at a rate of at most about 10%/min.

9. The method of claim 2 wherein said fatty acid coordinating ligand is oleic acid.

10. The method of claim 2 wherein said non-coordinating solvent is octadecene.

11. The nanocrystals of claim 1 being $NaYF_4$: $Er^{3+}/Yb^{3+}$ or $NaYF_4$: $Tm^{3+}/Yb^{3+}$.

12. The nanocrystals of claim 1 having a fatty acid coordinating ligand on a surface of said nanocrystals.

13. The nanocrystals of claim 12 wherein said fatty acid coordinating ligand is oleic acid.

14. The nanocrystals of claim 1 wherein said average particle size is between about 25 and about 35 nm.

15. The nanocrystals of claim 1 wherein said standard deviation is at most about 4%.

16. The nanocrystals of claim 1 wherein at least about 95% of the nanocrystal have a hexagonal shape when observed by Transmission Electron Microscopy (TEM).

17. The nanocrystals of claim 1 wherein said crystal are produced by a method comprising:
(a) providing a first solution comprising a non-coordinating solvent, a fatty acid coordinating ligand, sodium trifluoroacetate, yttrium trifluoroacetate, a first doping lanthanide trifluoroacetate and a second doping lanthanide trifluoroacetate, and a second solution comprising said non-coordinating solvent and said fatty acid coordinating ligand, said first and second solutions being substantially free of water and oxygen;
(b) in an inert atmosphere, slowly adding the first solution heated at a temperature between about 100° C. and about 150° C. to the second solution heated at temperature between about 290° C. and about 330° C., thereby producing a reaction mixture containing said nanocrystals;
(c) recovering said nanocrystals from said reaction mixture.

18. A method of identifying or authenticating a product, the method comprising the step of including the nanocrystals of claim 1 as a marker in said product.

19. The method of claim 18 wherein said product is an ink, a fuel, a paper, a cardboard, a polymer or a textile.

20. The method of claim 18, wherein said nanocrystals are produced by a method comprising:
(a) providing a first solution comprising a non-coordinating solvent, a fatty acid coordinating ligand, sodium trifluoroacetate, yttrium trifluoroacetate, a first doping lanthanide trifluoroacetate and a second doping lanthanide trifluoroacetate, and a second solution comprising said non-coordinating solvent and said fatty acid coordinating ligand, said first and second solutions being substantially free of water and oxygen;
(b) in an inert atmosphere, slowly adding the first solution heated at a temperature between about 100° C. and about 150° C. to the second solution heated at temperature between about 290° C. and about 330° C., thereby producing a reaction mixture containing said nanocrystals;
(c) recovering said nanocrystals from said reaction mixture.

21. A method of labelling an analyte, the method comprising contacting the analyte with the nanocrystals of claim 1, thereby permitting association of the analyte with the nanocrystals.

22. The method of claim 21, wherein said nanocrystals are produced by a method comprising:
(a) providing a first solution comprising a non-coordinating solvent, a fatty acid coordinating ligand, sodium trifluoroacetate, yttrium trifluoroacetate, a first doping lanthanide trifluoroacetate and a second doping lanthanide trifluoroacetate, and a second solution comprising said non-coordinating solvent and said fatty acid coordinating ligand, said first and second solutions being substantially free of water and oxygen;
(b) in an inert atmosphere, slowly adding the first solution heated at a temperature between about 100° C. and about 150° C. to the second solution heated at temperature between about 290° C. and about 330° C., thereby producing a reaction mixture containing said nanocrystals;
(c) recovering said nanocrystals from said reaction mixture.

23. The method of claim 21 wherein said nanocrystals are bound to said analyte.

24. The method of claim 21 wherein said analyte is a biological target.

25. A method of detecting an analyte, the method comprising:
(a) providing an analyte which is associated with the nanocrystals of claim 1; and
(b) detecting the analyte by stimulating the nanocrystals associated with the analyte.

26. The method of claim 25, wherein said providing step comprises contacting the analyte with the nanocrystals, thereby permitting association of the analyte with the nanocrystals.

27. The method of claim 25, wherein said nanocrystal are produced by a method comprising:
(a) providing a first solution comprising a non-coordinating solvent, a fatty acid coordinating ligand, sodium trifluoroacetate, yttrium trifluoroacetate, a first doping lanthanide trifluoroacetate and a second doping lanthanide trifluoroacetate, and a second solution comprising said non-coordinating solvent and said fatty acid coordinating ligand, said first and second solutions being substantially free of water and oxygen;
(b) in an inert atmosphere, slowly adding the first solution heated at a temperature between about 100° C. and about 150° C. to the second solution heated at temperature between about 290° C. and about 330° C., thereby producing a reaction mixture containing said nanocrystals;
(c) recovering said nanocrystals from said reaction mixture.

28. The method of claim 25 wherein said nanocrystals are bound to said analyte.

29. The method of claim 25 wherein said analyte is a biological target.

30. A method of producing a light source for the telecommunication industry, the method comprising the step of stimulating the nanocrystals of claim 1 with incoming light.

31. The method of claim 30, wherein said nanocrystal are produced by a method comprising:
(a) providing a first solution comprising a non-coordinating solvent, a fatty acid coordinating ligand, sodium trifluoroacetate, yttrium trifluoroacetate, a first doping lanthanide trifluoroacetate and a second doping lanthanide trifluoroacetate, and a second solution comprising said non-coordinating solvent and said fatty acid coordinating ligand, said first and second solutions being substantially free of water and oxygen;
(b) in an inert atmosphere, slowly adding the first solution heated at a temperature between about 100° C. and about 150° C. to the second solution heated at temperature between about 290° C. and about 330° C., thereby producing a reaction mixture containing said nanocrystals;
(c) recovering said nanocrystals from said reaction mixture.

* * * * *